(12) United States Patent
Rana et al.

(10) Patent No.: US 11,918,615 B2
(45) Date of Patent: *Mar. 5, 2024

(54) ANTI-INFLAMMATORY BOTANICAL EXTRACT

(71) Applicant: Innophos, LLC, Cranbury, NJ (US)

(72) Inventors: Jatinder Rana, Grand Rapids, MI (US); Kylie Mitchell, Pennington, NJ (US)

(73) Assignee: Innophos, LLC, Cranbury, NJ (US)

( * ) Notice: Subject to any disclaimer, the term of this patent is extended or adjusted under 35 U.S.C. 154(b) by 141 days.

This patent is subject to a terminal disclaimer.

(21) Appl. No.: 17/467,830

(22) Filed: Sep. 7, 2021

(65) Prior Publication Data
US 2022/0031788 A1   Feb. 3, 2022

Related U.S. Application Data

(62) Division of application No. 16/561,596, filed on Sep. 5, 2019, now Pat. No. 11,141,446.

(60) Provisional application No. 62/728,125, filed on Sep. 7, 2018.

(51) Int. Cl.
| | | |
|---|---|---|
| *A61K 36/45* | (2006.01) | |
| *A61K 9/00* | (2006.01) | |
| *A61K 31/353* | (2006.01) | |
| *A61P 29/00* | (2006.01) | |

(52) U.S. Cl.
CPC ............ *A61K 36/45* (2013.01); *A61K 9/0014* (2013.01); *A61K 9/0053* (2013.01); *A61K 31/353* (2013.01); *A61P 29/00* (2018.01)

(58) Field of Classification Search
None
See application file for complete search history.

(56) References Cited

U.S. PATENT DOCUMENTS 9,371,313 B2 *   6/2016   Woolford ............. A61K 31/352

* cited by examiner

*Primary Examiner* — Russell G Fiebig
(74) *Attorney, Agent, or Firm* — David LeCroy

(57) ABSTRACT

A botanical extract that exhibits anti-inflammatory activity, wherein the botanical extract is at least an extract from the leaf of *Vaccinium macrocarpon*.

7 Claims, 18 Drawing Sheets

Procyanidin A1　　　　　　　　Procyanidin A2

Procyanidin B1;EC (4β→8)-C　　　　Procyanidin B5;EC (4β→8)-EC
Procyanidin B2;EC (4β→8)-EC　　　Procyanidin B6;C-(4α→8)-C
Procyanidin B3;C-(4α→8)-C　　　　Procyanidin B7;BC (4β→8)-C
Procyanidin B4;C-(4α→8)-EC　　　 Procyanidin B8;C- (4α→8)-EC Quercetin　　　　　　　　　　Isoquercetin 6'-O-trans-Caffeoylarbutin　　　　Avicularin Procyanidin A1

Procyanidin A2

Procyanidin B1;EC (4β→8)-C
Procyanidin B2;EC (4β→8)-EC
Procyanidin B3;C (4α→8)-C
Procyanidin B4;C (4α→8)-EC Procyanidin B5;EC (4β→6)-EC
Procyanidin B6;C (4α→6)-C
Procyanidin B7;BC (4β→6)-C
Procyanidin B8;C (4α→6)-EC Monotropein, 6,7-Dihydro,
10-O-(4-hydroxy-e-cinnamayl)

Myricetin 3-arabinofuranoside

6'-O-trans-Caffeoylarbutin

Avircularin

1. Cyanidin-3-galactoside (R=Gal)
2. Cyanidin-3-arabinoside (R=Ara)

3. Peonidin-3-galactoside (R=Gal)
4. Peonidin-3-arabinoside (R=Ara)

5. Malvidin-3-galactoside (R=Gal)

ANTI-INFLAMMATORY BOTANICAL EXTRACT

CROSS REFERENCE TO RELATED APPLICATIONS

The present application is a divisional application of U.S. Pat. No. 11,141,446, issued 12 Oct. 2021, which claims the benefit of U.S. Patent Application No. 62/728,125, filed 7 Sep. 2018, the disclosure of which is incorporated herein in its entirety by reference.

BACKGROUND OF THE INVENTION

Field of the Invention. The present invention generally relates to a botanical extract that exhibits anti-inflammatory activity, namely, cranberry (*Vaccinium macrocarpon*) leaves, and compositions comprising such an extract.

Arachidonic acid and its metabolites are important mediators of inflammation. Arachidonic acid ('AA') is a component of membrane phospholipids where the rate-limiting step in the formation of its metabolites depends on its release from the cell membrane phospholipid pool mediated through activation of phospholipases. Thereafter, it can be metabolized by one of two pathways—by cyclooxygenase ('COX') to yield eicosanoids such as prostaglandins ('PGE2'), prostacyclins, and thromboxanes, or it can be metabolized by 5-lipoxygenase ('5-LOX') to result in the production of leukotrienes and lipoxins. These eicosanoids serve as intracellular messengers and play significant roles in the regulation of signal transduction in pain and inflammatory responses. An illustration of the arachidonic acid metabolism pathway is provided in FIGS. 1A and 1B.

Cyclooxygenase—a prostanoid synthase also known as prostaglandin-endoperoxide synthase (PTGS, EC 1.14.99.1)—is an enzyme that is responsible for the formation of important biological mediators called prostanoids, including prostaglandins, prostacyclin and thromboxane. COX is the central enzyme in the biosynthetic pathway to prostanoids from arachidonic acid. There are two known isoenzymes—COX-1 and COX-2. COX-1 represents the constitutive isoform responsible for production of prostaglandins involved in physiological functions such as protection of the gastric mucosa and maintenance of renal perfusion. COX-2 is not expressed under normal conditions in most cells, but elevated levels are found during inflammation. COX-2 is the dominant isozyme in inflamed tissues, where its induction can be facilitated by several pro-inflammatory cytokines, including interleukin-1 (IL-1') and tumor necrosis factor (TNF-α'). Pharmacological inhibition of COX by non-steroidal anti-inflammatory drugs (NSAID) can provide relief from the symptoms of inflammation and pain.

Therefore, to prevent the unwanted side effects, it seems practical to inhibit COX-2 selectively for its analgesic and anti-inflammatory effects without affecting important physiological processes controlled by the prostaglandins formed by COX-1. Still, there are reports that associate the synergistic effect of COX-2 as a constitutive isoenzyme in maintaining renal blood flow and the glomerular filtration rate suggesting its selective inhibition may lead to some adverse effects. These effects were experienced by subjects in clinical trials wherein selective COX-2 inhibitors (e.g., celecoxib and rofecoxib) provided similar efficacy to that of traditional NSAIDs in osteoarthritis and rheumatoid arthritis pain with better gastric tolerability and equivalent to NSAIDs in renal side effects. Therefore, it is reasonable to assume and have a compound strong enough to cause inhibition of these isoenzymes yet moderate enough to avoid the unnecessary adverse consequences, as opposed to a complete selective inhibition of either of the enzymes.

Increased expression of COX-2, and hence synthesis of its product PGE2, has also been found to be strongly associated with the induction of MMP-9, which is a key player in cancer, cardiovascular disease, and inflammation. Therefore, inhibition of COX-2 enzyme may result in regulation of MMP-9 expression and activity that may modulate invasion and migration of cancer cells, prevent or delay the progression of atherosclerosis and stabilize plaques, regulate macrophage proteinase expression, prevent chronic periodontitis and gingivitis, and control remodeling of liver disease, among others.

The other segment of the Arachidonic acid ('AA') metabolism pathway is through the 5-lipoxygenase ('5-LOX') pathway, where leukotrienes (LTB4, LTC4, LTD4, and LTE4) derived from LTA4 are the end bioactive metabolites. LTC4 and its products LTD4 and LTE4 act on smooth muscle cells of bronchi and blood vessels, where their biologic effects suggest their role in allergic reaction and inflammatory processes. For example, in asthma they cause bronchoconstriction, vasoconstriction, and increased vascular permeability; thus, they are previously known as slow-reacting substances of anaphylaxis. The other component of this pathway—LTB4—is a potent chemotactic factor of neutrophils. While the specific inhibitor of the 5-LOX enzyme—Zileuton—provides effective intervention of asthma attacks where the anti-inflammatory and antibronchospastic effects work together, single therapeutic modality for 5-LOX modulators seems insufficient.

Preferably, anti-inflammatory products encompass inhibition of both main metabolic pathways of Arachidonic acid ('AA') metabolism, possessing a wide range of anti-inflammatory activities while also having a better safety profile.

Another mediator of inflammation which acts as cytokine and is secreted by immune cells are High Mobility Group Box 1 proteins ('HMGB1'), also known as high-mobility group protein 1 ('HMG-1') and amphoterin. HMGB1 is a protein that in humans is encoded by the HMGB1 gene. Like the histones, HMGB1 is among the most important chromatin proteins. HMGB1 is a 30 kDa nuclear and cytosolic protein and is a self-derived immune activator that has multiple functions in the regulation of immunity and inflammation.

HMGB1 can be released actively by innate immune cells such as macrophages, monocytes, and dendritic cells at the time of inflammation and injury. For example, macrophages and monocytes actively release HMGB1 in a time- and dose-dependent manner in response to stimulation with exogenous bacterial endotoxin (e.g., lipopolysaccharide, or LPS), or endogenous pro-inflammatory cytokines such as tumor necrosis factor ('TNF-α'), Interleukin-1 beta (IL-1β'), and Interferon gamma ('IFN-γ').

HMGB1 can also be released passively by necrotic or damaged cells and is capable of inducing an inflammatory response by communicating the insult to the neighboring immune cells, allowing the innate immune cells to both respond to injury and to further induce inflammation. HMGB1 proteins trigger intracellular signaling through receptor for advanced glycosylation end products ('RAGE') and/or Toll-like receptors (TLR-2/4), which in turn activate various signaling pathways as mitogen-activated protein kinase ('MARK') pathways and subsequent nuclear factor kappa-light-chain-enhancer of activated B cells ('NF-κB')

mediating inflammation, leading to the expression of various leukocyte adhesion molecules, pro-inflammatory cytokines, and chemokines.

HMGB1 plays significant roles in inflammatory activity and is involved in a wide range of immune responses. HMGB1 induces maturation and migration of dendritic cells ('DCs'), as well as the activation of these cells and monocytes to produce pro-inflammatory cytokines such as TNF-α, IL-1β, IL-6, and macrophage inflammatory protein 1 ('MIP-1'). HMGB1 also serves as a chemotactic factor for monocytes, macrophages, neutrophils, and DCs to sustain inflammation and elicit innate immune response.

HMGB1 is considered a lead example of a danger signal that originates from the damaged self instead of from invading pathogens. HMGB1 mediates activation of innate receptors resulting in the amplification of inflammatory responses through the release of cytokines, which in turn induce the release of additional HMGB1, further promoting the induction of these mediators. While pro-inflammatory cytokines such as TNF-α, IL-1β, and IFN-γ are known to mediate the early phases of inflammation, HMGB1 is considered as the late phase dictator in sepsis and tissue injury.

Targeting HMGB1 may be a pragmatic approach for therapeutic interventions in inflammatory diseases as it has been identified as a crucial mediator in the pathogenesis of many diseases, including sepsis, arthritis, cancer, and diabetes. For example, the level of HMGB1 has been found to be elevated in (1) synovial fluid of patients with rheumatoid arthritis, (2) septic patients who did not survive compared to those who did survive, (3) invasion and metastasis of solid tumors, and (4) diabetes and its complications.

As a consequence, many pharmacologic agents have been studied for their potential to inhibit release of HMGB1 or HMGB1 activity (see, FIG. 2). These include traditional herbal medicines such as aqueous extracts of dong guai or dang gui ("female ginseng"—Angelica sinensis), Green tea (Camellia sisensis), and Danshen ("red sage" or "Chinese sage"—Saliva miltorrhiza), which have been found to inhibit endotoxin-induced HMGB1 release, as well as protect animals against experimental sepsis.

Accordingly, phytomedicine plays an important role in the management of most of these diseases, with plants being a potential source of natural antioxidants. Studies have shown that the consumption of polyphenolic compounds found in tea, herbs, fruits, and vegetables is associated with low risk of these diseases. Consequently, there is a growing research interest in plants that exhibit anti-inflammatory activity and health-promoting phytoconstituents as potential therapeutic agents. Medicinal plants can provide a safe, cost-effective, ecological alternative to chemical antioxidants, which can be toxic on prolonged exposure.

Cranberry (Vaccinium macrocarpon) was introduced to European settlers by Native Americans, who used the berries for treating kidney stones and urinary tract health problems. Since then, cranberry has been used to treat a variety of ailments, including urinary tract infections, stomach ailments, scurvy, vomiting, and weight loss by a large portion of the North American population. There are a number of cranberry fruit extracts on the market, and cranberry fruit juice is a common and popular beverage alone or in combination with other juices. Further, there is excellent recognition by the public of the health benefits of cranberry fruit-based products.

A strong body of scientific research documents the contribution of the consumption of berries to the three targets of functional foods: (a) health maintenance; (b) reduced risk of obesity; and (c) reduced risk of chronic diet-related diseases (e.g., cardiovascular disease, type 2 diabetes, and metabolic syndrome). In addition to the fruits, the leaves of berry plants have been used in traditional remedies. Leaf extracts have often been used against several diseases, such as colds, urinary tract inflammation, diabetes, and ocular dysfunction by Native Americans and other populations.

Still, little is known about the composition of leaves of berry plants and their beneficial properties. It is known that the main bioactive compounds in berry leaves are similar to those found in their fruits (i.e., phenolic acids and esters, flavanols, anthocyanins, and procyanidins). It is also known that the concentrations of these compounds can vary from family to family within the genera Vaccinium.

As noted above, there is a need for effective, nontoxic, natural compounds with anti-inflammatory activity. The present invention provides one such solution.

BRIEF SUMMARY OF THE INVENTION

Disclosed herein is a composition comprising the botanical extract of the leaf of Vaccinium macrocarpon, wherein the botanical extract exhibits anti-inflammatory activity. The the botanical extract can be present in the composition an amount of about 1.0 µg/mL or greater. Preferably, the botanical extract is present in an amount of about 1.0 µg/mL to about 2000.0 µg/mL; more preferably, in an amount of about 50.0 µg/mL to about 500.0 µg/mL.

In one aspect, the composition inhibits COX-1 activity. In such instances, the botanical extract is present in the composition in an amount of about 50.0 µg/mL to about 500.0 µg/mL.

In a further aspect, the composition inhibits COX-2 activity. In such instances, the botanical extract is present in the composition in an amount of about 30.0 µg/mL to about 500.0 µg/mL.

In another aspect, the composition inhibits 5-LOX activity. In such instances, the botanical extract is present in the composition in an amount of about 60.0 µg/mL to about 250.0 µg/mL.

In another aspect, the composition comprising the botanical extract of the leaf of Vaccinium macrocarpon inhibits COX-1 activity, COX-2 activity, and 5-LOX activity.

The composition comprising the botanical extract of the leaf of Vaccinium macrocarpon can also contain a pharmaceutically acceptable carrier. The composition can be in the form of a dietary supplement. In another embodiment, the composition is a topical composition.

The present invention further provides for a dietary supplement having anti-inflammatory properties comprising a cranberry leaf extract in a therapeutically effective amount.

The present invention also provides a method of inhibiting inflammation in a subject comprising administering a composition comprising the botanical extract of the leaf of Vaccinium macrocarpon at a concentration of about 1.0 µg/mL to about 2000.0 µg/mL. Preferably, the botanical extract is present in an amount of about 1.0 µg/mL to about 2000.0 µg/mL; more preferably, in an amount of about 50.0 µg/mL to about 500.0 µg/mL.

DETAILED DESCRIPTION OF THE INVENTION

Figure 1A:
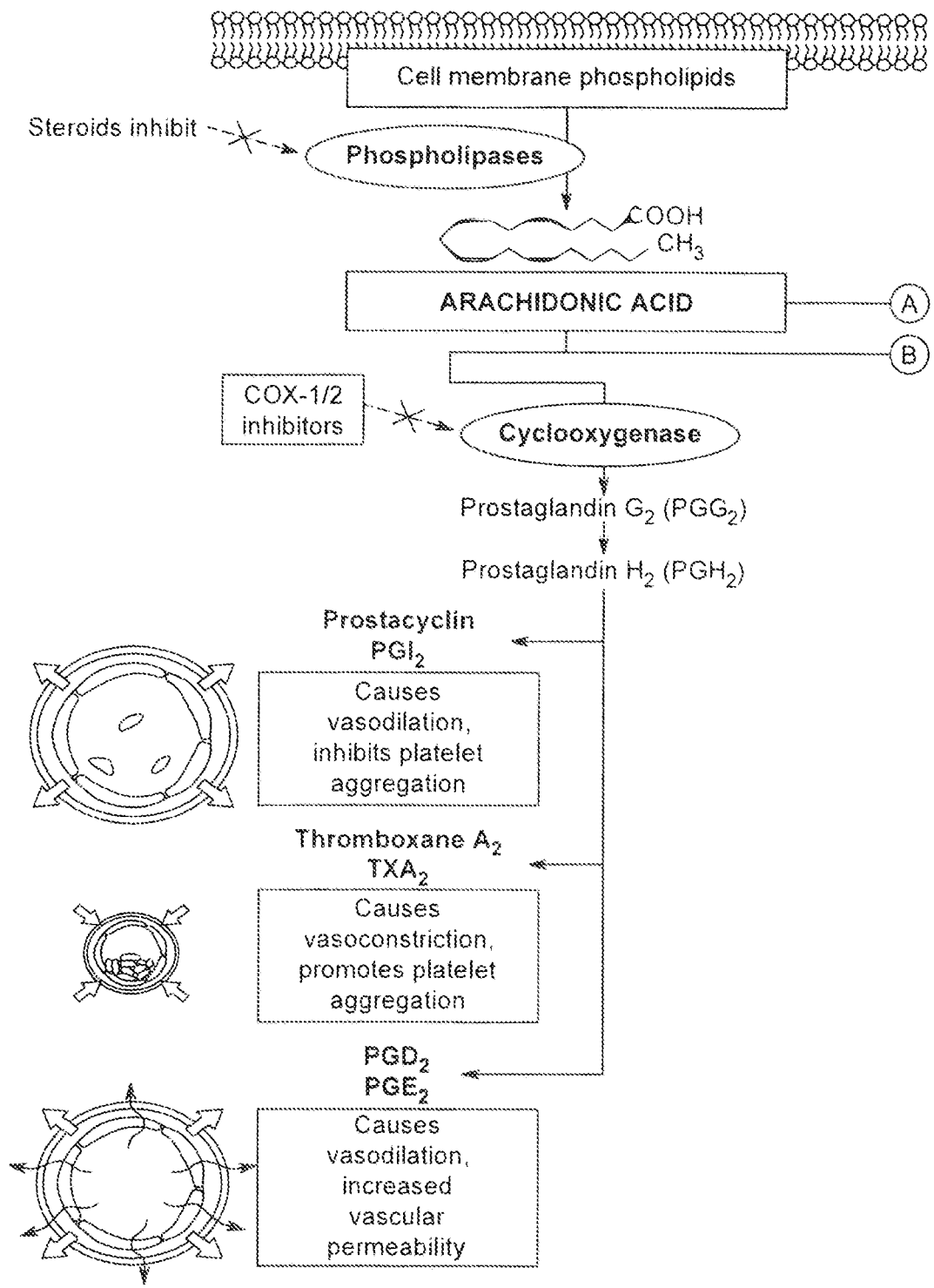
FIGS. 1A and 1B is a general illustration of the Arachidonic acid metabolism pathway.
Figure 1B:
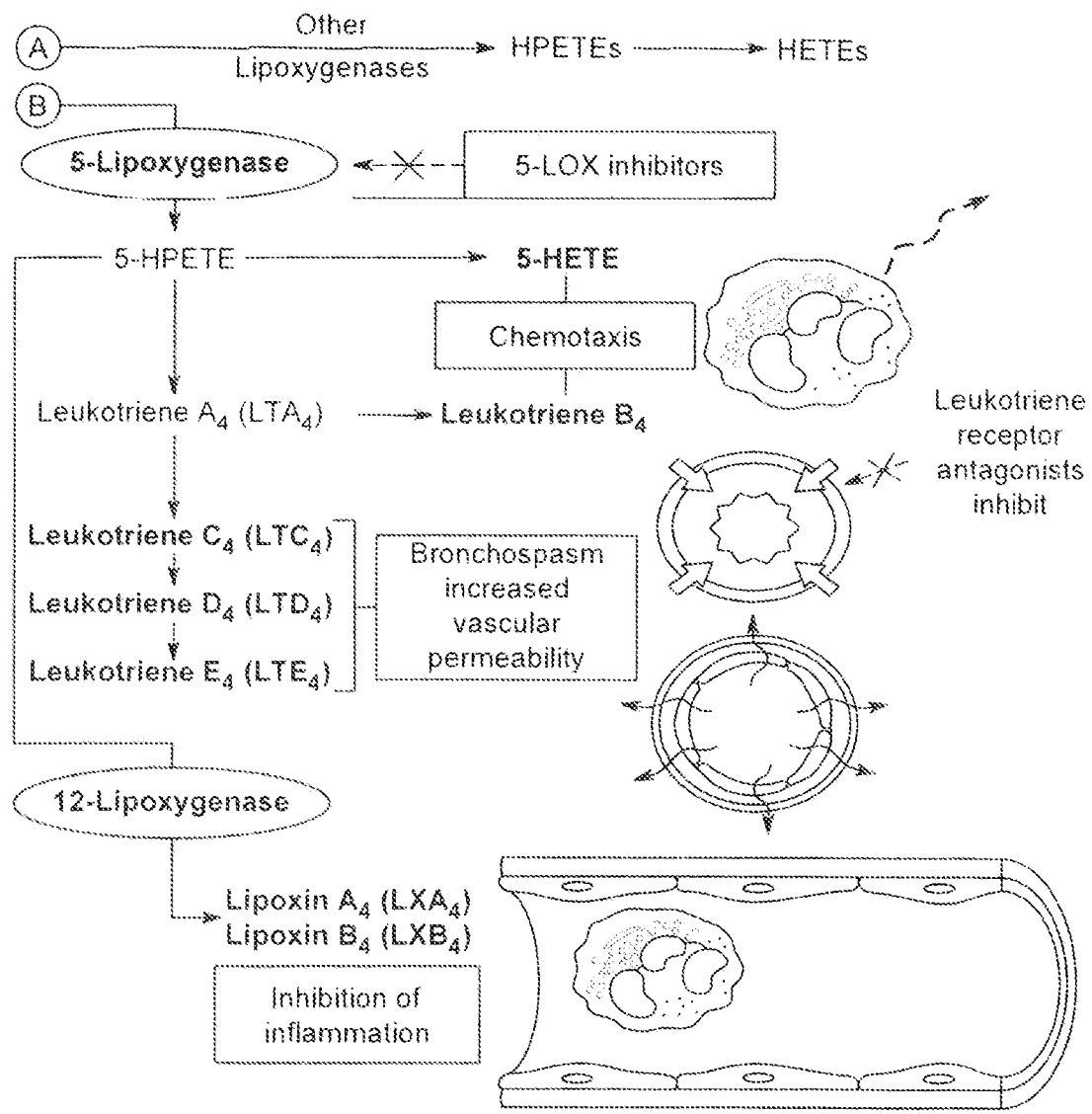
Figure 2:
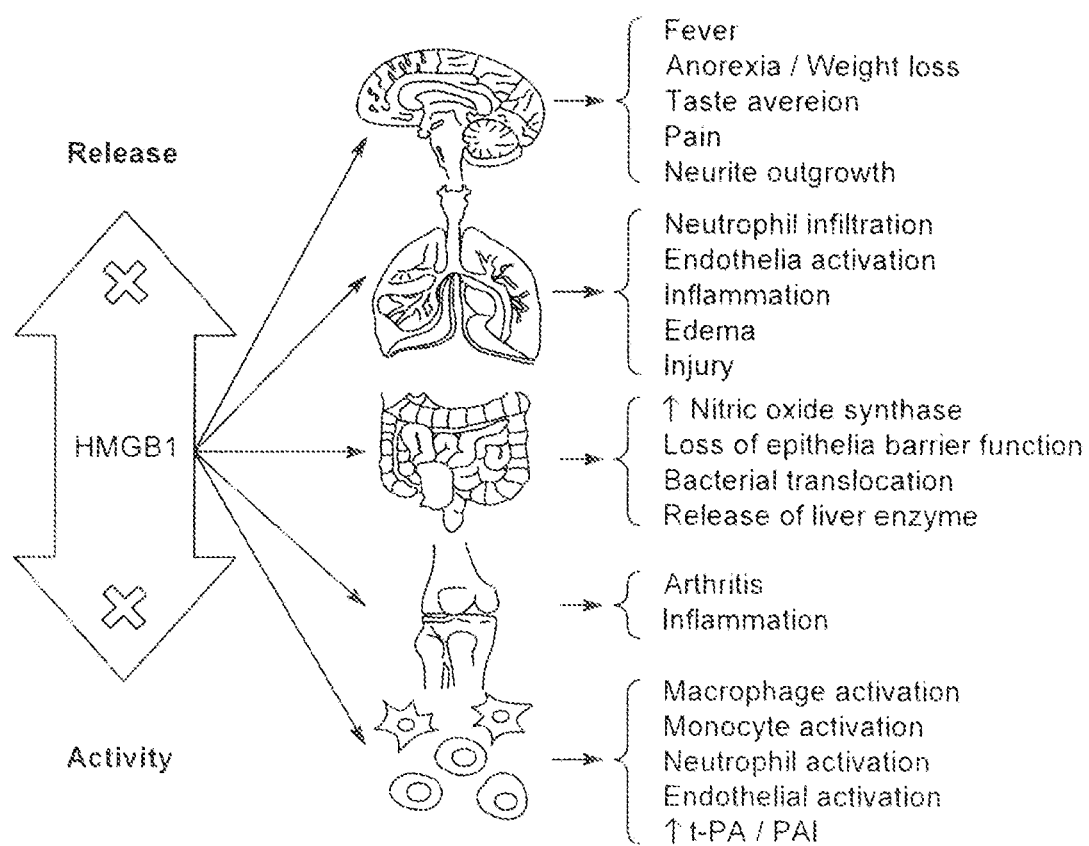
FIG. 2 is a general illustration of HMGB1-mediated pro-inflammatory responses at various sites.
Figure 3A:
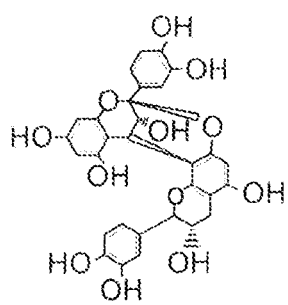
FIGS. 3A and 3B provides the chemical structures of various procyanidin and flavonoid compounds identified in cranberry fruit extract (E1) (non-exhaustive).
Figure 3A:
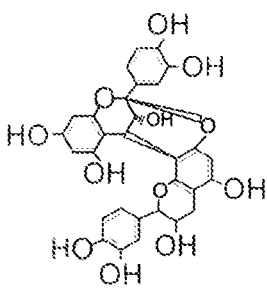
Figure 3A:
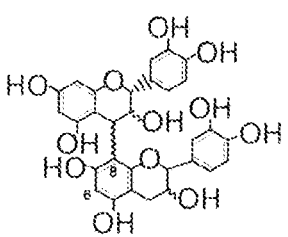
Figure 3A:
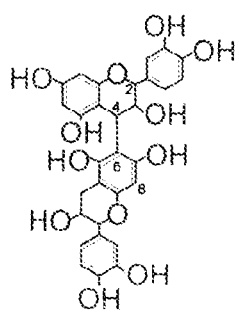
Figure 3A:
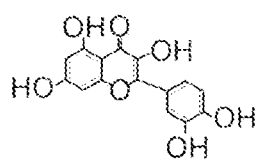
Figure 3A:
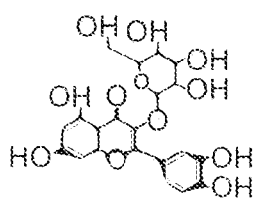
Figure 3A:
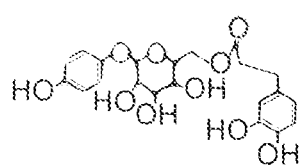
Figure 3A:
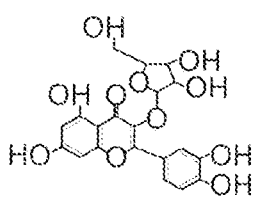
Figure 3B:
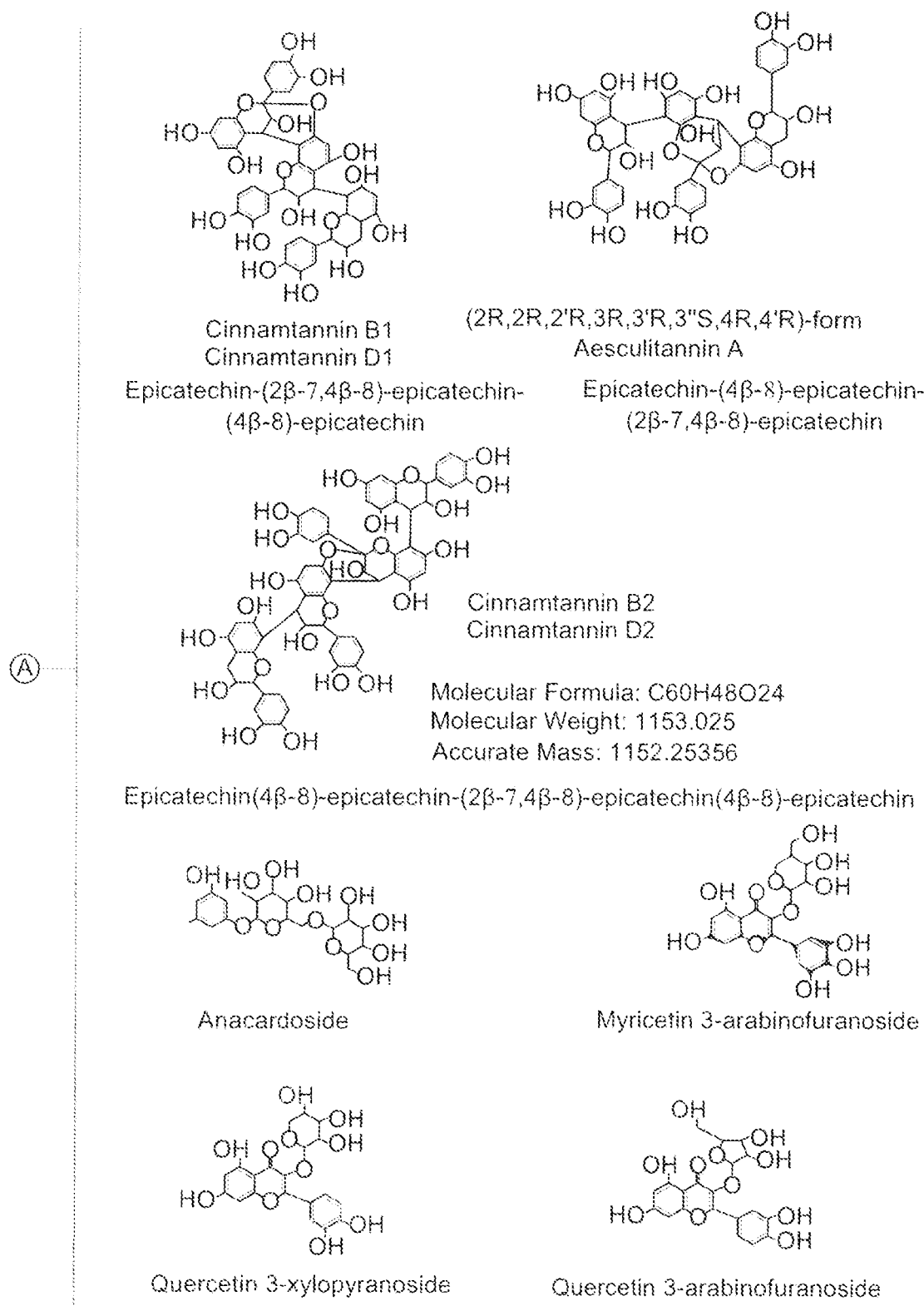
Figure 4A:
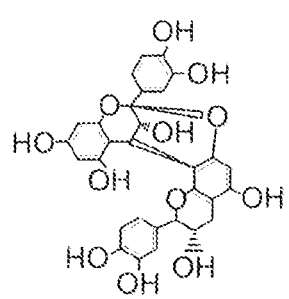
FIGS. 4A and 4B provides the chemical structures of various procyanidin and flavonoid compounds identified in cranberry leaf extract (E2) (non-exhaustive).
Figure 4A:
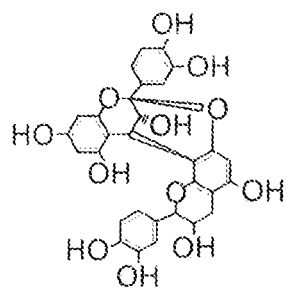
Figure 4A:
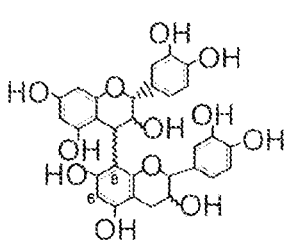
Figure 4A:
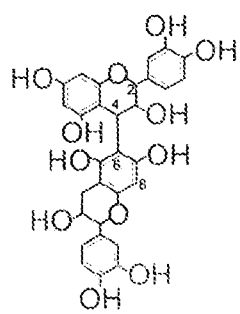
Figure 4A:
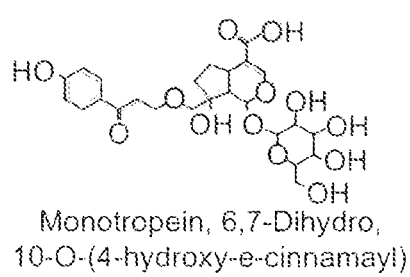
Figure 4A:
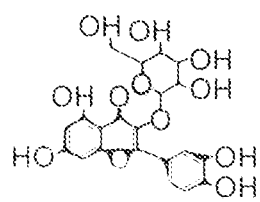
Figure 4A:
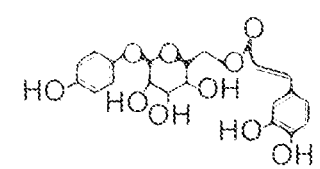
Figure 4A:
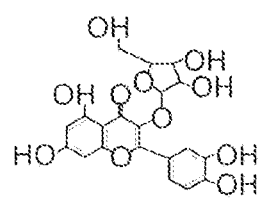
Figure 4B:
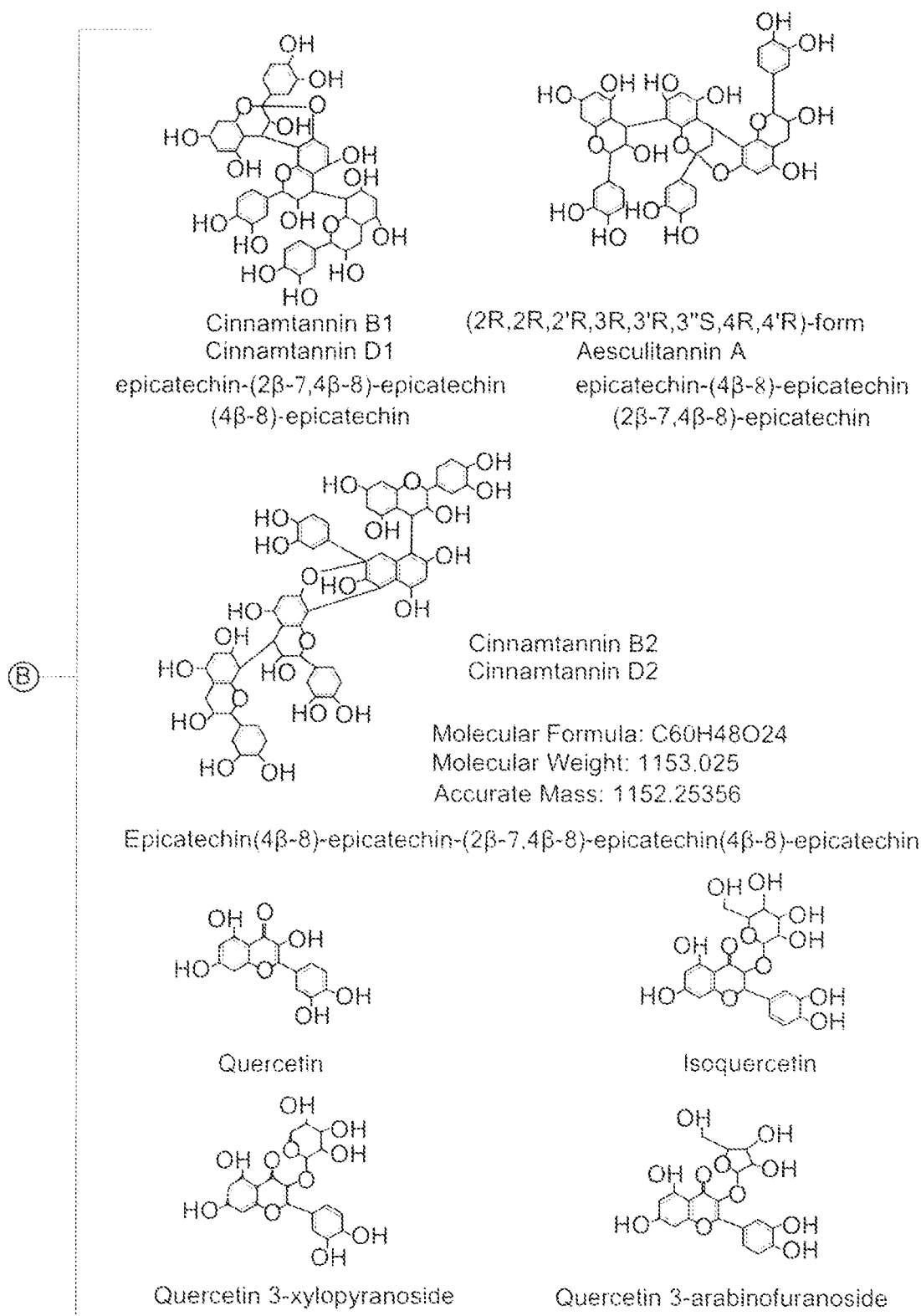

Disclosed herein is a botanical extract of the fruit and/or leaf of a plant comprising multiple procyanidins and bioflavonoids, wherein the fruit extract has been standardized to an anthocyanin content of about 1.90 mg/g, based on total weight of cyanidin-3-galactoside, cyaniding-3-arabinoside, peonidin-3-galactoside, peonidin-3-arabinoside, and malvidin-3-galactoside in the fruit extract, and wherein the botanical extract comprises at least an extract from the genus *Vaccinium*. Data noted herein demonstrates that cranberry leaf extract may have anti-inflammatory applications.

The present invention is further based on the surprising discovery that the leaf of the cranberry plant (*Vaccinium macrocarpon*) is substantially higher in certain flavonoids than the cranberry fruit. In particular, the extract from the leaves has a flavonoid content of at least 20 times greater than the flavonoid content of the fruit of the cranberry plant. In another embodiment, the extract from the leaves comprises a procyanidin trimers and procyanidin tetramers content of at least 23 times and 700 times greater than the procyanidin trimers and procyanidin tetramers content, respectively, of the fruit of the cranberry plant. Accordingly, in one embodiment, the botanical extract is from at least the leaves of *Vaccinium macrocarpon*. Further, the botanical extract from at least the leaves of *Vaccinium macrocarpon* may have anti-inflammatory applications.

When the botanical extract is at least the leaf of the plant, the botanical extract can be present in the composition in an amount of about 1.0 µg/mL or greater. For example, the leaf extract can be present in the composition in an amount of about 1.0 µg/mL to about 1000.0 µg/mL.

For the present application, the term "composition" refers to a product that treats, improves, promotes, increases, manages, controls, maintains, optimizes, modifies, reduces, inhibits, or prevents a particular condition associated with a natural state, biological process or disease or disorder. For example, a composition improves the inhibition of oxidation and/or reduces inflammation, and the like in a subject. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment. Compositions can also include beverages, for example, beverages infused with an effective amount of an extract, or a tea satchel containing an effective amount of an extract. Non-limiting examples of food compositions containing an effective amount of an extract include baked goods, protein powders, meat products, dairy products, and confectionary.

As used herein, the term "extract" or "botanical extract" refers to a solid, viscid, or liquid substance or preparation that includes one or more active ingredients of a substance of at least the plant *Vaccinium* (e.g., *Vaccinium macrocarpon* and/or *Vaccinium oxycoccos*). Preferably, the active ingredient is derived from the extract of the leaf of the plant. The extract can be prepared using a solvent such as water, lower alcohols of 1 to 4 carbon atoms (e.g., methanol, ethanol, butanol, etc.), ethylene, acetone, hexane, ether, chloroform, ethylacetate, butylacetate, dichloromethane, N,N-dimethylformamide (DMF'), dimethylsulfoxide ('DMSO'), 1,3-butylene glycol, propylene glycol, and combinations thereof, but also a fraction of the crude extract in such a solvent. So long as it assures the extraction and preservation of the active ingredient(s), any extraction method may be employed.

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving the inhibition of oxidation and/or reducing inflammation, and the like in a subject. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer", "administered", "administers", and "administering" are defined as providing a composition to a subject via a route known in the art, including but not limited to intravenous, intra-arterial, oral, parenteral, buccal, topical, transdermal, rectal, intramuscular, subcutaneous, intraosseous, transmucosal, or intraperitoneal routes of administration. In preferred embodiments, oral routes of administering a composition are suitable.

As used herein, the term "subject" or "individual" includes mammals to which a composition may be administered. Non-limiting examples of mammals include humans, non-human primates, canines, felines, equines, bovines, rodents (including transgenic and non-transgenic mice) or the like. In some embodiments, the subject is a non-human mammal, and in some embodiments, the subject is human.

As used herein, the term "carrier" refers to a composition that aids in maintaining one or more plant extracts in a soluble and homogeneous state in a form suitable for administration, which is nontoxic, and which does not interact with other components in a deleterious manner.

Unless indicated otherwise, all proportions and percentages recited throughout this disclosure are by weight.

The present invention provides a botanical extract that exhibits anti-inflammatory activity. More particularly, the present invention is directed towards a botanical extract of the leaves of the cranberry plant from the genus *Vaccinium*. Such botanical extracts have been found to exhibit anti-inflammatory activity.

As previously stated, useful anti-inflammatory botanical extracts according to the present invention include botanical extracts from the genus *Vaccinium*. More particularly, the botanical extract can be obtained from a plant chosen from *Vaccinium arctostaphylos, Vaccinium macrocarpon, Vaccinium oxycoccos, Vaccinium microcarpum, Vaccinium microcarpum, Vaccinium erythrocarpum, Vaccinium arboretum, Vaccinium crassifolium, Vaccinium angustifolium, Vaccinium boreale, Vaccinium caesariense, Vaccinium caespitosum, Vaccinium corymbosum, Vaccinium darrowii, Vaccinium deliciosum, Vaccinium elliotii, Vaccinium floribundum, Vaccinium hirsutum, Vaccinium membranaceum, Vaccinium myrsinites, Vaccinium myrtilloides, Vaccinium myrtillus, Vaccinium ovalifolium, Vaccinium ovatum, Vaccinium padifolium, Vaccinium pallidum, Vaccinium parvifolium, Vaccinium praestans, Vaccinium reticulatum, Vaccinium scoparium, Vaccinium stamineum, Vaccinium tenellum, Vaccinium uliginosum, Vaccinium virgatum*, and/ or *Vaccinium vitis-idaea*. Preferably, the botanical extract is at least from *Vaccinium macrocarpon, Vaccinium oxycoccos, Vaccinium microcarpum*, and/or *Vaccinium microcarpum*. More preferably, the botanical extract is at least from *Vaccinium macrocarpon*; even more preferably a botanical extract from the leaf of *Vaccinium macrocarpon*.

Anti-inflammatory compositions according to the present invention may include one or more compounds that may function as active ingredients and which are a component of the botanical extract. For example, the compound can be a phytochemical present in the plant from which the plant extract is obtained. The compound may be at least partially responsible for exhibiting anti-inflammatory activity. The compound can be any compound capable of inhibiting inflammation. In one embodiment, the compound is chosen from the phytochemicals isoquercetin, quercetin-3-glycoside, kaempferol glycoside, and/or procyanidins (e.g., A, B, trimer, tetramer).

Generally, one or more parts of a plant can be used to produce a plant extract including, but not limited to, the root, the stem, the leaf, the flower, the fruit, the seed, and the testa of the seed. In the present invention, at least the leaf of the plant is used—alone or with other plant parts, particularly the fruit—to produce the plant extract. The fruit and leaf from the *Vaccinium* plant can be commercially obtained from various sources. The extract of the fruit and leaf can be obtained using any suitable extraction technique.

In this regard, one or more parts of the plant, particularly the leaf of the *Vaccinium* plant, can be collected and milled. Thereafter, the milled material can be extracted using a suitable solvent. The solvent can be removed in a concentration step. For example, the extracted material can be screened or filtered to create a supernatant and a cake. The cake can be pressed to remove a substantial portion of the liquid, which can be added to the supernatant. The cake can then be dehydrated and used as a fiber source. The supernatant can be distilled to remove the solvent or a portion thereof, to form a plant extract liquid concentrate. The removed solvent can be recycled. The concentrate can be dried (e.g., by spray drying) to provide a dried plant extract. This dried plant extract can be assayed and/or standardized as described herein. Preferably, the dried plant extract is derived from *Vaccinium macrocarpon*, particularly the leaf of the plant *Vaccinium macrocarpon*.

Suitable solvents for the extraction process include water, alcohol, or mixtures thereof. Exemplary alcoholic solvents include, but are not limited to, $C_1$-$C_7$ alcohols (e.g., methanol, ethanol, propanol, isopropanol, and butanol), hydroalcohols or mixtures of alcohol and water (e.g., hydroethanol), polyhydric alcohols (e.g., propylene glycol and butylene glycol), and fatty alcohols. Any of these alcoholic solvents can be used in the form of a mixture. In one embodiment, the plant extract is extracted using ethanol, water, or a combination thereof (e.g., a mixture of about 70% ethanol and about 30% water). In another embodiment, the plant extract is extracted using only water.

In one embodiment, the plant extract can be obtained using an organic solvent extraction technique. In another embodiment, solvent sequential fractionation can be used to obtain the plant extract. Total hydro-ethanolic extraction techniques can also be used to obtain the plant extract. Generally, this is referred to as a lump-sum extraction.

Total ethanol extraction can also be used. This technique uses ethanol as the solvent. This extraction technique can generate a plant extract having fat soluble and/or lipophilic compounds in addition to water soluble compounds.

Another example of an extraction technique that can be used to obtain the plant extract is supercritical fluid extraction ('SFE'). In this extraction procedure, the material to be extracted may not be exposed to any organic solvents. Rather, carbon dioxide can be used as the extraction solvent—with or without a modifier—in super-critical conditions (>31.3° C. and >73.8 bar). Those skilled in the art will appreciate that temperature and pressure conditions can be varied to obtain the best yield of extract. This technique can generate an extract of fat soluble and/or lipophilic compounds, similar to a total hexane and ethyl acetate extraction technique.

The botanical extract generated in the process can include a broad variety of phytochemicals present in the extracted material. The phytochemicals can be fat soluble or water soluble. Following collection of the extract solution, the solvent can be evaporated, resulting in the extract.

The botanical extract can be standardized to a specified amount of a particular compound. For example, the plant extract can be standardized to a specified amount of an active ingredient or phytochemical.

The amount of plant extract present in the inflammation inhibiting composition can depend upon several factors, including the desired level of inflammation inhibition, the inflammation inhibiting level of a particular plant extract or component thereof, and other factors. Preferably, the plant extract is present in an amount of from about 0.005 wt % or greater, for example, from about 0.005 wt % to about 99.00 wt %, based on total weight of the composition.

The anti-inflammatory composition can include one or more acceptable carriers. The carrier can aid in enabling incorporation of the plant extract into an anti-inflammatory composition having a suitable form for administration to a subject. A wide number of acceptable carriers are known in the art, and the carrier can be any suitable carrier. The carrier is preferable suitable for administration to animals, including humans, and can be able to act as a carrier without substantially affecting the desired activity of the plant extract and/or any active ingredient. The carrier can be chosen based upon the desired administration route and dosage form of the composition.

Suitable dosage forms include liquid and solid forms. In one embodiment, the composition is in the form of a gel, a syrup, a slurry, or a suspension. In another embodiment, the composition is in a liquid dosage form such as a drink shot or a liquid concentrate. In a further embodiment, the composition is present in a solid dosage form, such as a tablet, a pill, a capsule, a dragée, or a powder. When in liquid or solid dosage form, the composition can be in a food delivery form suitable for incorporation into food for delivery. Examples of suitable carriers for use in solid forms (particularly tablet and capsule forms) include, but are not limited to, organic and inorganic inert carrier materials such as gelatin, starch, magnesium stearate, talc, gums, silicon dioxide, stearic acid, cellulose, and the like. The carrier can be substantially inert.

As an example, silicified microcrystalline cellulose can be used as a carrier or binder. Silicified microcrystalline cellulose is a physical mixture of microcrystalline cellulose and colloidal silicon dioxide. One such suitable form of silicified microcrystalline cellulose is ProSolv SMCC® 90, available from Penwest Pharmaceutical Co., Patterson, N.J. Silicon dioxide, in addition to that provided by the silicified microcrystalline cellulose, may be added to the composition as a processing aid. For example, silicon dioxide can be included as a glidant to improve the flow of powder during compression in the manufacturing of solid dosage units, such as tablet.

In another embodiment, the carrier is at least a functional carrier such as buckwheat or spelt. By the addition of functional carriers into the composition, additional benefits may be provided such as lower glycemic index compared to standard carriers such as those mentioned above. Further, functional carriers can be allergen free (e.g., buckwheat), and by adding them into the production process, the botanical extracts of the invention may benefit from the flavonoids of these functional carriers, such as rutin and quercetin. Further, the high fiber content of these functional carriers may also facilitate and regulate intestinal transit. Finally, the added mineral benefit of selenium found in spelt may aid in metabolism.

The anti-inflammatory composition can include other inert ingredients, such as lubricants and/or glidants. Lubricants aid in the handling of tablets during manufacturing, such as during ejection from dies. Glidants improve powder flow during tablet compression. Stearic acid is an example of an acceptable lubricant/glidant.

The anti-inflammatory composition can be made in solid dosage form, such as tablets and capsules. This form provides a product that can be easily transported by an individual to a place of eating, such as a restaurant, and taken prior to, during, or after consumption of a foodstuff. The composition can be formulated into dosage units containing suitable amounts of the plant extract and/or active ingredient that permit an individual to determine an appropriate number of units to take based upon appropriate parameters, such as body weight, foodstuff size, or carbohydrate (e.g., sugar) content.

In one embodiment, the botanical extract is present in the composition in a therapeutically effective amount, such as an amount of about 1.0 µg/mL or greater, preferably from about 1.0 µg/mL to about 2000.0 µg/mL, more preferably from about 50.0 µg/mL to about 500.0 µg/mL. The composition can be administered, for example, in a dosage of from about 1.0 µg/mL to about 2000.0 µg/mL per day of the plant extract. The composition can be administered as a single dose, or in multiple doses. In one example, the compound is administered in up to three doses per day. For example, the compound may be administered prior to a meal, during a meal, or after a meal. In one embodiment, the composition is a dietary supplement having anti-inflammatory properties containing cranberry leaf extract in a therapeutically effective amount.

The dosage can be chosen to provide a level of inhibitory effect in a single unit that may be effective for some individuals and/or some foodstuffs, while also allowing for relatively simple dosage increases to provide other levels of inhibitory effects that can be effective for other individuals and/or other foodstuffs.

The inhibiting composition can be in a form adapted for oral ingestion. This form can be configured as a single dosage form intended to provide a specified dose of the plant extract. For example, the single dosage form can be a powder, a pill, a tablet, a capsule, or a drink shot. The single dosage form can include, for example, from about 1.0 µg/mL to about 2000.0 µg/mL of the plant extract.

EXAMPLES

Examples—Materials and Chemical Profiling

Example 1—Preparation of 70% Ethanol Extracts from Cranberry Fruit and Cranberry Leaf Dried cranberry fruit powder (*Vaccinium macrocarpon*) (60 g) was loaded into three 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was automatically filtered and collected. The combined ethanol extract solution was evaporated with a rotary evaporator under vacuum to give a crude 70% ethanol fruit extract (EP).

Dried ground cranberry leaf powder (*Vaccinium macrocarpon*) (140 g) was loaded into seven 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was automatically filtered and collected. The combined ethanol extract solution was evaporated with a rotary evaporator under vacuum to give a crude 70% ethanol leaf extract ('E2').

The extraction results are provided in the following Table 1—

TABLE 1

Extraction of Cranberry fruit E1 and Cranberry leaf E2

| Plant Part | Extract ID | Plant Powder (g) | Extract Weight (g) | Extraction Yield (wt %) |
|---|---|---|---|---|
| Fruit | E1 | 60 | 27.40 | 45.67% |
| Leaf | E2 | 140 | 23.75 | 16.96% |

Example 2—Chemistry Profiling of Cranberry Fruit E1 and Cranberry Leaf E2 Extracts Flavonoid compounds present in the cranberry fruit extract E1 and cranberry leaf extract E2 were determined using ultra high-pressure liquid chromatography ('HPLC') and mass spectrometry (ACQUITY® UPLC I-Class and XEVO® GS-XT-QTof system, both available from Water Corporation, Milford, Massachusetts USA). The column used was an ACQUITY® UPLC HSS T3 2.1×100 mm, 1.8 with a column temperature of 40° C. and a sample temperature of 15° C. For the mobile phase, Solvent A was 10% acetonitrile ('ACN') in water (0.1% Formic Acid), and Solvent B was ACN. The acquisition range was 100-1500 Daltons ('Da'), and the acquisition mode was electrospray ionization ('ESI') (−). Table 2 below provides the HPLC conditions—

TABLE 2

HPLC condition for analyzing E1 and E2 extracts

| Extract | Run Time (min) | Injection Volume (μL) | Concentration |
|---|---|---|---|
| E1 | 20.00 | 1.00 | 5 mg/mL |
| E2 | 20.00 | 2.00 | 1 mg/mL |

Peak identification was based on accurate mass only. Multiple isomers may have been identified as the same compound due to the limitation of the database. For example, eight (8) procyanidin B1-B8 compounds having the same molecular weight of 578.528 were not differentiated in this analysis.

Procyanidins and flavonoid glycosides such as quercetin, isoquercetin, and myricetin 3-arabinofuranoside were detected and identified based on accurate mass in E1 at relatively low content. Chemical structures of compounds detected in E1 (non-exhaustive) are illustrated in FIG. 3. The following table lists compounds identified in E1 based on accurate mass—

TABLE 3

Compounds Identified in E1

| Compound Name | Neutral Mass (Da) | Observed Neutral Mass (Da) | Observed m/z | Mass error (ppm) | Observed RT (min) | Detector counts |
|---|---|---|---|---|---|---|
| Vaccihein A | 378.09508 | 378.0935 | 377.0862 | −4.3 | 0.65 | 22406 |
| Procyanidin B | 578.14243 | 578.1445 | 577.1373 | 3.6 | 0.66 | 13886 |
| 8-[5-(3,4-Dihydroxy-7-hydroxy-4-oxo-2H-1-benzopyran-2-yl)-2-hydroxyphenyl]-2,3-dihydro-7-hydroxy-2-(4-hydroxyphenyl)-4H-1-benzopyran-4-one | 510.13147 | 510.1291 | 509.1218 | −4.7 | 0.68 | 21507 |
| Procyanidin trimer | 864.19016 | 864.1939 | 863.1867 | 4.4 | 0.72 | 19512 |
| Monotropein | 390.11621 | 390.1165 | 389.1092 | 0.8 | 0.93 | 7503 |
| Orcinol gentiobioside, Anacardioside | 448.15808 | 448.1574 | 447.1501 | −1.6 | 3.20 | 22920 |
| 2-O-Benzoylglucose; D-form | 284.08960 | 284.0894 | 283.0822 | −0.6 | 3.54 | 18514 |
| Leptosin | 462.11621 | 462.1164 | 461.1091 | 0.4 | 3.59 | 51758 |
| Leptosin | 462.11621 | 462.1164 | 461.1091 | 0.4 | 3.63 | 38344 |
| 2-O-Benzoylglucose; D-form | 284.08960 | 284.0893 | 283.0820 | −1.0 | 3.71 | 6747 |
| Procyanidin trimer | 864.19016 | 864.1872 | 863.1800 | −3.4 | 3.79 | 5716 |
| Dunalianoside B | 450.11621 | 450.1150 | 449.1077 | −2.7 | 3.95 | 7628 |
| Dunalianoside B | 450.11621 | 450.1147 | 449.1074 | −3.5 | 4.12 | 7014 |
| Procyanidin trimer | 864.19016 | 864.1862 | 863.1789 | −4.6 | 4.15 | 45918 |
| 2-O-Benzoylglucose; D-form | 284.08960 | 284.0891 | 283.0819 | −1.6 | 4.17 | 6085 |
| Procyanidin tetramer | 1152.25355 | 1152.2530 | 1151.2457 | −0.5 | 4.37 | 5523 |
| Procyanidin trimer | 864.19016 | 864.1866 | 863.1793 | −4.1 | 4.98 | 5966 |
| Myricetin 3-arabinofuranoside | 450.07983 | 450.0793 | 449.0721 | −1.1 | 5.17 | 8296 |
| Myricetin 3-arabinofuranoside | 450.07983 | 450.0795 | 449.0723 | −0.6 | 5.51 | 16797 |
| Myricetin 3-arabinofuranoside | 450.07983 | 450.0803 | 449.0730 | 1.0 | 5.64 | 46613 |
| Vaccinoside | 536.15299 | 536.1530 | 535.1457 | 0.0 | 5.78 | 28664 |
| Vaccinoside | 536.15299 | 536.1533 | 535.1460 | 0.6 | 5.97 | 72372 |
| Procyanidin A | 576.12678 | 576.1274 | 575.1201 | 1.1 | 6.13 | 119550 |
| Monotropein; 6,7-Dihydro,10-O-(4-hydroxy-E-cinnamoyl) | 538.16864 | 538.1692 | 537.1620 | 1.1 | 6.16 | 57726 |
| Monotropein; 6,7-Dihydro,10-O-(4-hydroxy-E-cinnamoyl) | 538.16864 | 538.1699 | 537.1626 | 2.4 | 6.33 | 151522 |
| Vaccinoside | 536.15299 | 536.1536 | 535.1463 | 1.1 | 6.35 | 7992 |
| Avicularin | 434.08491 | 434.0858 | 433.0785 | 2.0 | 6.38 | 62923 |
| Vaccinoside | 536.15299 | 536.1534 | 535.1461 | 0.7 | 6.46 | 5222 |
| Avicularin | 434.08491 | 434.0860 | 433.0787 | 2.5 | 6.56 | 52683 |

TABLE 3-continued

Compounds Identified in E1

| Compound Name | Neutral Mass (Da) | Observed Neutral Mass (Da) | Observed m/z | Mass error (ppm) | Observed RT (min) | Detector counts |
|---|---|---|---|---|---|---|
| Avicularin | 434.08491 | 434.0859 | 433.0787 | 2.4 | 6.79 | 130113 |
| Myricetin 3'-methyl ether | 332.05322 | 332.0536 | 331.0463 | 1.1 | 9.83 | 10303 |
| 4-O-Acetyl-6-trans-caffeoylarbutin | 476.13186 | 476.1319 | 475.1247 | 0.1 | 12.14 | 12950 |

Abundant bioflavonoids were identified in E2, including avicularin, isoquercetin, kaempferol, glycosides, and others. Chemical structures of compounds detected in E2 (non-exhaustive) are illustrated in FIG. 4. The following table lists compounds identified in E2 based on accurate mass—

TABLE 4

Compounds Identified in E2

| Compound Name | Neutral Mass (Da) | Observed Neutral Mass (Da) | Observed m/z | Mass error (ppm) | Observed RT (min) | Detector counts |
|---|---|---|---|---|---|---|
| Procyanidin B | 578.14243 | 578.1441 | 577.1368 | 2.8 | 0.67 | 13416 |
| Monotropein | 390.11621 | 390.1155 | 389.1082 | −1.8 | 0.72 | 31923 |
| Procyanidin trimer | 864.19016 | 864.1872 | 863.1799 | −3.4 | 0.75 | 9024 |
| Procyanidin tetramer | 1152.25355 | 1152.2512 | 1151.2439 | −2.0 | 0.75 | 33165 |
| Myricetin 3-arabinofuranoside | 450.07983 | 450.0792 | 449.0720 | −1.3 | 0.94 | 6589 |
| Monotropein | 390.11621 | 390.1166 | 389.1093 | 0.9 | 0.94 | 43918 |
| Procyanidin tetramer | 1152.25355 | 1152.2502 | 1151.2429 | −2.9 | 2.36 | 28086 |
| Procyanidin B | 578.14243 | 578.1411 | 577.1338 | −2.3 | 3.19 | 10152 |
| Orcinol gentiobioside, Anacardioside | 448.15808 | 448.1582 | 447.1510 | 0.3 | 3.19 | 480731 |
| Procyanidin trimer | 864.19016 | 864.1878 | 863.1806 | −2.7 | 3.25 | 104158 |
| Procyanidin tetramer | 1152.25355 | 1152.2502 | 1151.2429 | −2.9 | 3.28 | 34709 |
| Procyanidin A | 576.12678 | 576.1260 | 575.1188 | −1.3 | 3.29 | 6558 |
| Procyanidin B | 578.14243 | 578.1418 | 577.1345 | −1.2 | 3.35 | 31488 |
| Orcinol gentiobioside | 448.15808 | 448.1581 | 447.1508 | 0.1 | 3.41 | 55958 |
| Procyanidin tetramer | 1152.25355 | 1152.2493 | 1151.2420 | −3.7 | 3.60 | 22964 |
| Orcinol gentiobioside, Anacardioside | 448.15808 | 448.1574 | 447.1501 | −1.5 | 3.63 | 9322 |
| Procyanidin trimer | 864.19016 | 864.1872 | 863.1799 | −3.5 | 3.80 | 53828 |
| Dunalianoside B | 450.11621 | 450.1157 | 449.1084 | −1.2 | 3.94 | 20828 |
| Procyanidin trimer | 864.19016 | 864.1883 | 863.1811 | −2.1 | 4.16 | 262966 |
| Procyanidin tetramer | 1152.25355 | 1152.2507 | 1151.2434 | −2.5 | 4.38 | 89683 |
| Procyanidin A | 576.12678 | 576.1261 | 575.1188 | −1.2 | 4.38 | 13405 |
| Procyanidin trimer | 864.19016 | 864.1870 | 863.1797 | −3.6 | 4.54 | 9939 |
| Procyanidin trimer | 864.19016 | 864.1885 | 863.1812 | −2.0 | 4.98 | 98041 |
| Procyanidin A | 576.12678 | 576.1262 | 575.1190 | −0.9 | 4.99 | 9959 |
| Procyanidin A | 576.12678 | 576.1257 | 575.1185 | −1.8 | 5.10 | 22194 |
| Procyanidin tetramer | 1152.25355 | 1152.2495 | 1151.2423 | −3.5 | 5.14 | 21067 |
| Procyanidin tetramer | 1152.25355 | 1152.2490 | 1151.2417 | −4.0 | 5.26 | 14044 |
| Procyanidin A | 576.12678 | 576.1264 | 575.1191 | −0.7 | 5.26 | 7671 |
| Procyanidin trimer | 864.19016 | 864.1871 | 863.1798 | −3.6 | 5.34 | 9598 |
| Procyanidin A | 576.12678 | 576.1173 | 575.1173 | −3.8 | 5.47 | 6853 |
| Procyanidin tetramer | 1152.25355 | 1152.2491 | 1151.2419 | −3.8 | 5.47 | 17471 |
| Procyanidin trimer | 864.19016 | 864.1873 | 863.1800 | −3.3 | 5.53 | 11401 |
| Myricetin 3-arabinofuranoside | 450.07983 | 450.0804 | 449.0732 | 1.4 | 5.63 | 22203 |
| Vaccinoside | 536.15299 | 536.1531 | 535.1458 | 0.1 | 5.78 | 98913 |
| Dunalianoside B | 450.11621 | 450.1164 | 449.1091 | 0.4 | 5.83 | 5653 |
| Vaccinoside | 536.15299 | 536.1531 | 535.1459 | 0.3 | 5.97 | 153237 |
| Procyanidin A | 576.12678 | 576.1275 | 575.1202 | 1.3 | 6.12 | 398543 |
| Procyanidin tetramer | 1152.25355 | 1152.2502 | 1151.2429 | −2.9 | 6.12 | 35819 |
| Jeediflavanone | 558.11621 | 558.1170 | 557.1097 | 1.4 | 6.12 | 5855 |
| Monotropein; 6,7-Dihydro,10-O-(4-hydroxy-E-cinnamoyl) | 538.16864 | 538.1696 | 537.1623 | 1.7 | 6.15 | 208791 |
| Procyanidin trimer | 864.19016 | 864.1890 | 863.1817 | −1.4 | 6.20 | 65398 |
| Monotropein; 6,7-Dihydro,10-O-(4-hydroxy-E-cinnamoyl) | 538.16864 | 538.1693 | 537.1620 | 1.2 | 6.33 | 353675 |
| Vaccinoside | 536.15299 | 536.1530 | 535.1457 | 0.0 | 6.35 | 6705 |
| Avicularin | 434.08491 | 434.0857 | 433.0785 | 1.9 | 6.38 | 512642 |
| Vaccinoside | 536.15299 | 536.1545 | 535.1472 | 2.8 | 6.47 | 9321 |
| Procyanidin A | 576.12678 | 576.1265 | 575.1192 | −0.5 | 6.47 | 11610 |
| Procyanidin tetramer | 1152.25355 | 1152.2511 | 1151.2438 | −2.1 | 6.47 | 33495 |
| Procyanidin trimer | 864.19016 | 864.1892 | 863.1819 | −1.1 | 6.48 | 113767 |
| Avicularin | 434.08491 | 434.0859 | 433.0787 | 2.4 | 6.56 | 916754 |

TABLE 4-continued

Compounds Identified in E2

| Compound Name | Neutral Mass (Da) | Observed Neutral Mass (Da) | Observed m/z | Mass error (ppm) | Observed RT (min) | Detector counts |
|---|---|---|---|---|---|---|
| 4-Hydroxyphenyl-gentioside | 434.14243 | 434.1441 | 433.1368 | 3.8 | 6.56 | 7559 |
| 3',4',4''',5',7,7''-Hexahydroxy-8,3'''-biflavanone | 542.12130 | 542.1229 | 541.1156 | 3.0 | 6.59 | 7805 |
| 3,5-Bis(3,4-dihydroxycinnamoyl)quinic acide | 516.12678 | 516.1259 | 515.1186 | −1.7 | 6.61 | 6367 |
| Avicularin | 434.08491 | 434.0859 | 433.0786 | 2.2 | 6.78 | 1907961 |
| 2,4,6-Trihydroxyphenylacetic acid; 2-O-(3,4-Dihydroxybenzoyl) | 320.05322 | 320.0541 | 319.0468 | 2.6 | 7.08 | 8233 |
| Dunalianoside B | 450.11621 | 450.1165 | 449.1092 | 0.6 | 7.42 | 19468 |
| Procyanidin A | 576.12678 | 576.1246 | 575.1173 | −3.9 | 7.49 | 6252 |
| Lyonside | 552.22068 | 552.2212 | 551.2139 | 0.9 | 7.50 | 42922 |
| Quercetin 3-glycosides; Monosaccharides, 3-O-[3-Hydroxy-3-methylglutaroyl-(4)-1 ± L-rhamnopyranoside | 592.14282 | 592.1432 | 591.1359 | 0.7 | 7.73 | 15267 |
| Leptosin | 462.11621 | 462.1171 | 461.1098 | 1.9 | 8.39 | 5097 |
| 8-[5-(3,4-Dihydroxy-7-hydroxy-4-oxo-2H-1-benzopyran-2-yl)-2-hydroxyphenyl]-2,3-dihydro-7-hydroxy-2-(4-hydroxyphenyl)-4H-1-benzopyran-4-one | 510.13147 | 510.1324 | 509.1251 | 1.8 | 8.63 | 8411 |
| Lyoniside | 552.22068 | 552.2210 | 551.2138 | 0.6 | 8.73 | 6492 |
| Procyanidin A | 576.12678 | 576.1270 | 575.1197 | 0.4 | 8.86 | 8440 |
| Procyanidin B | 578.14243 | 578.1420 | 577.1347 | −0.8 | 12.84 | 7997 |

Multiple procyanidins were found in E2 at substantially higher content compared to E1. Procyanidin dimers—including both A and B types—were found to be about fifty (50) times higher in E2 compared to E1 based on detector counts with mass-to-charge ratio ('m/z') at 575.11 and 577.13. Procyanidin trimers with observed m/z at 863.18 were present at about twenty-three (23) times higher in E2 compared to E1, whereas procyanidin tetramer with m/z at 1152.24 was over seven hundred (700) times higher in E2 compared to E1.

Similar bioflavonoids were also identified in E2 with much higher abundance, including isoquercetin, quercetin-3-arabinofuranoside, kaempferol glycoside, etc. based on LCMS analysis. Flavonoids with observed m/z at 463.093—identified with molecular formula $C_{21}H_{22}O_{10}$—are twenty (20) times higher for peak with retention time ('RT') at 6.38 min, and thirty-six (36) times higher for peak with RT at 6.78 min for E2 compared to corresponding peaks detected in E1. Overall detector counts of flavonoids in E2 are over twenty (20) times higher than flavonoids in E1 based on LCMS analysis.

Figure 5:
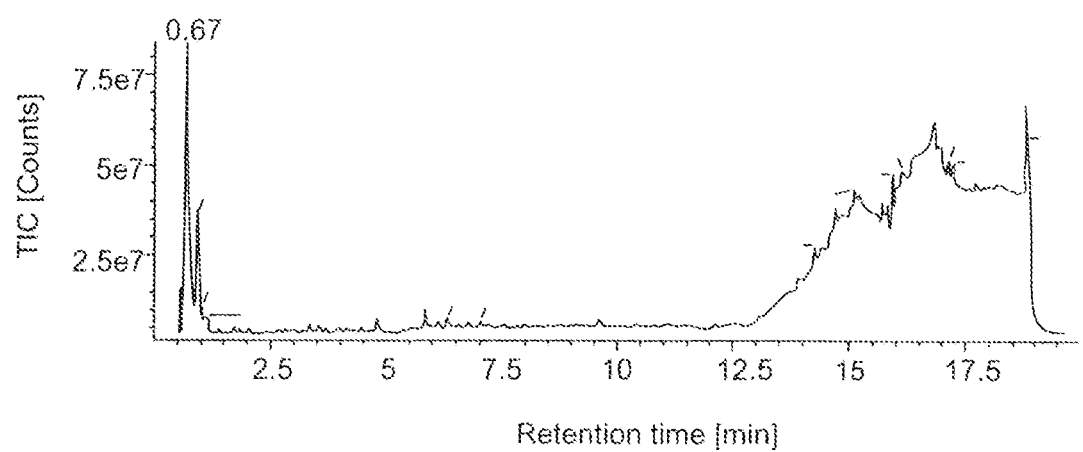
FIG. 5 is an LC/MS TIC chromatogram of cranberry fruit extract (E1).
Figure 6:
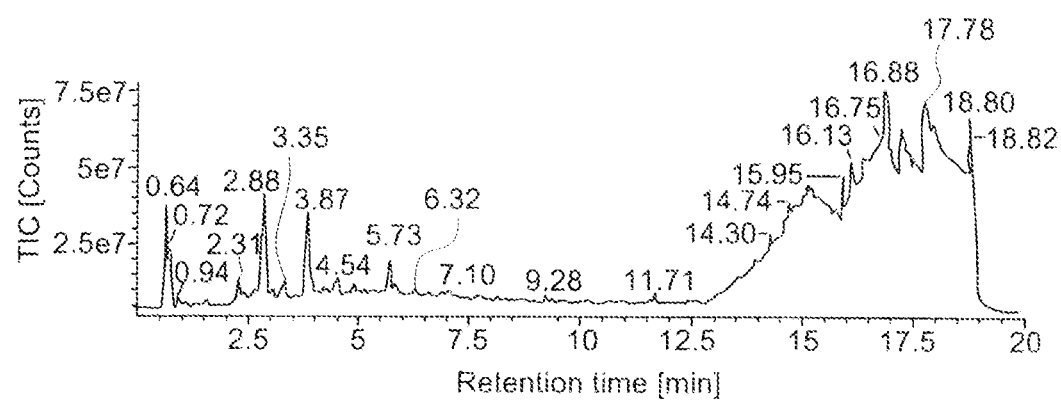
FIG. 6 is an LC/MS TIC chromatogram of cranberry leaf extract (E2).
Figure 7:
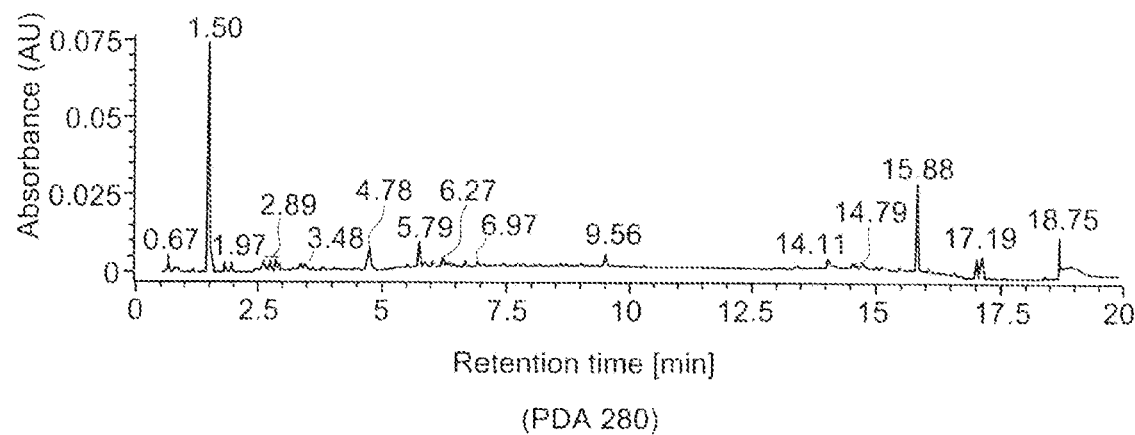
FIG. 7 is LC/PDA (wavelengths of 280 and 350 nm) chromatograms of cranberry fruit extract (E1).
Figure 7:
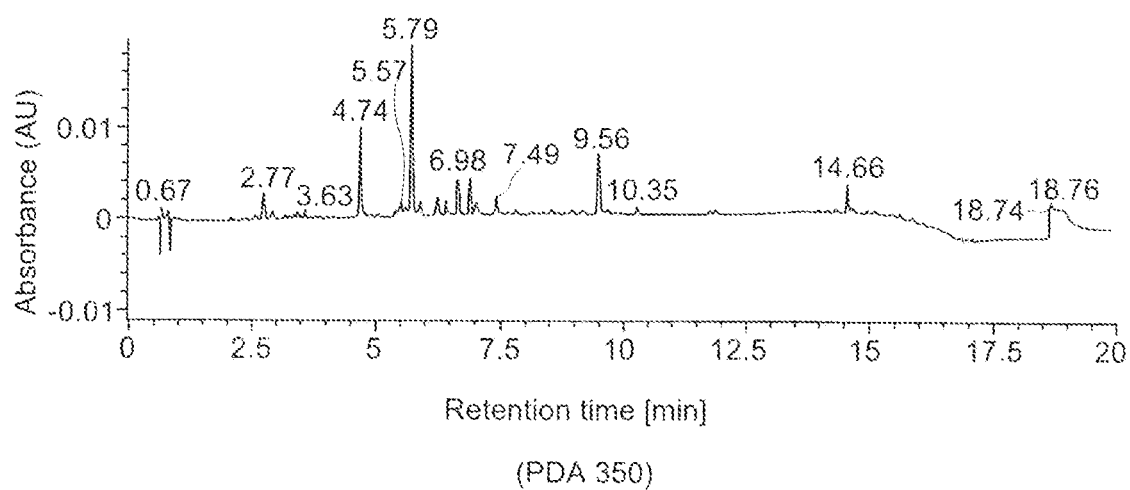
Figure 8:
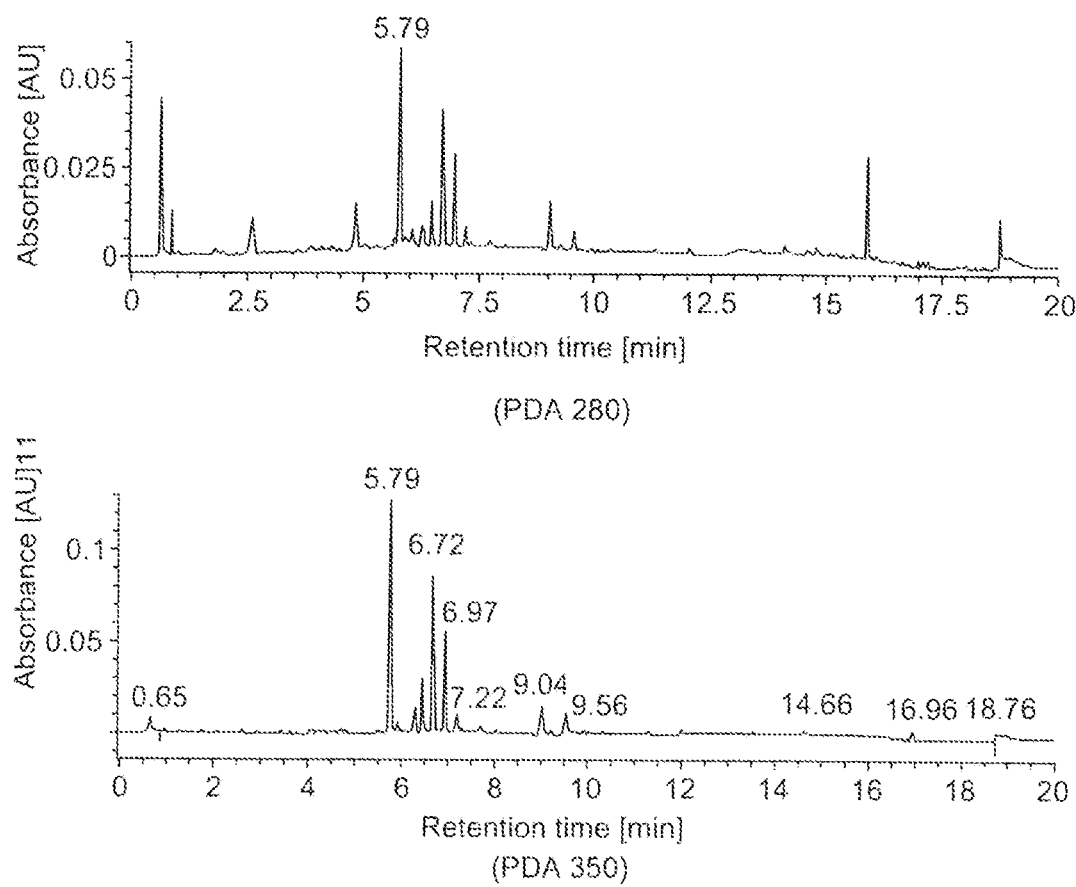
FIG. 8 is LC/PDA (wavelengths of 280 and 350 nm) chromatograms of cranberry leaf extract (E2).
Figure 9:
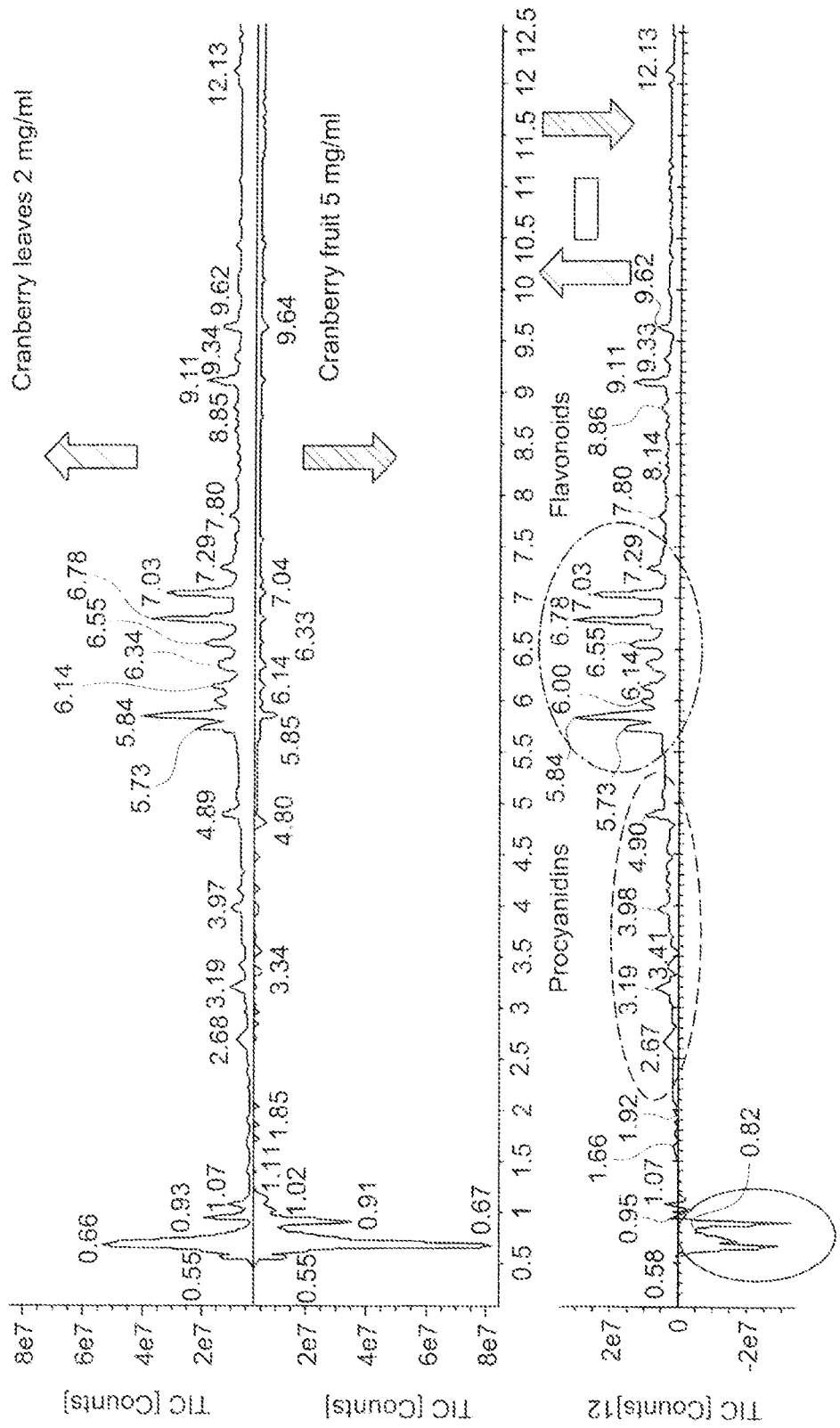
FIG. 9 is LC/MS TIC chromatograms comparison between cranberry fruit extract (E1) and cranberry leaf extract (E2).

LCMS TIC, PDA 280 nm, and PDA 350 nm chromatograms are provided in FIGS. 5 and 7 for E1 and FIGS. 6 and 8 for E2. LCMS TIC chromatograms comparison between E2 and E1—illustrated in FIG. 9—clearly showed the higher contents for procyanidins and bioflavonoids in E2, while higher organic acid content was seen in E1.

Example 3—Anthocyanins Quantification

Anthocyanins quantification method was adapted from published HPLC analytical method (J. AERIC. FOOD CHEM., "Separation, identification, quantification, and method validation of anthocyanins in botanical supplement raw materials by HPLC and HPLC-MS", Vol. 49(8), pp. 3515-3521 (2001)). HPLC system used was an Hitachi D7000 HPLC system, with a Phenomenex Luna 10 μm C18 column having a column size of 4.6×250 mm. Solvents used in the mobile phase were 0.5% phosphoric acid in $H_2O$ (Solvent A) and $H_2O$/ACN/Acetic Acid/$H_3PO_4$ (50%:48.5%:1.0%:0.5%) (Solvent B). UV wavelength was 480 nm.

Reference standard cyanidin-3-glucoside was purchased from ChromaDex (Chicago, Illinois US). Cyanidin-3glucoside was prepared at 1 mg/mL concentration in 2% (v/v) HCl in methanol solution in 5 mL volumetric flask. The stock solution was further diluted by ⅕, 1/10, 1/20, and 1/100 times in 2% (v/v) HCl in methanol to give cyanidin-3-glucoside solutions at five concentrations of 1.00, 0.20, 0.10, 0.05 and 0.01 mg/mL, respectively. The five solutions were unitized to generate a calibration curve. Each sample was injected at 10 μL in three replicates. The calibration curve was determined based on the integrated peak areas. The correlation coefficient (R2) value of cyanidin-3-glucoside was determined at 0.9985.

Figure 11:
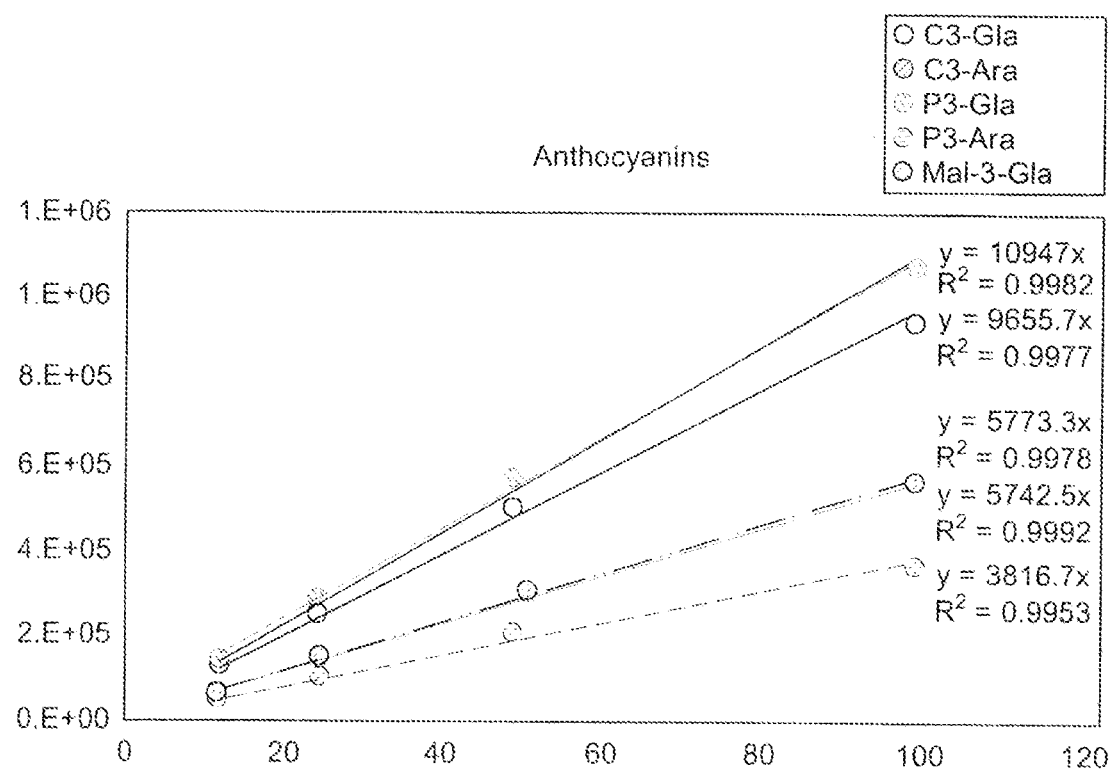
FIG. 11 is an illustration of the calibration curves of anthocyanins in cranberry fruit extract (E1).

Samples were prepared for analysis as follows. 12.5, 25.0, 50.0, and 100.0 mg of E1 were weighed. 1 mL of 2% (v/v) HCl in methanol was added to each sample, and then each sample was mixed by sonication for fifteen (15) minutes and vortexed at 10,000 rpm for five (5) minutes. 20 μL of supernatant of each solution was injected to HPLC in three replicates. Quantitative analysis of five (5) anthocyanin compounds at different concentrations demonstrated linearity with correlation coefficients $R^2$ from 0.9953 to 0.9982 (FIG. 11). The amount of each individual anthocyanin was calculated based on the integrated peak areas against cyaniding-3-glucoside at 0.05 mg/mL for the samples at a concentration of 25 mg/mL and 50 mg/mL, respectively.

Five anthocyanins were quantified in E1with a total content of 1.903 mg/g as of dry weight of E1. These anthocyanins included Cyanidin-3-galactoside ('C3Gla'), Cyanidin-3-arabinoside ('C3-Ara'), Peonidin-3-galactoside ('P3-Gla'), Peonidin-3-arabinoside ('P3-Ara'), and Malvidin-3-galactoside (Ma13-Gla'), based on analysis and comparison with those disclosed in the analytical method article and the article J. AOAC INT., "Determination of anthocyanins in Cranberry fruit and Cranberry fruit products by High-Performance Liquid Chromatography with Ultraviolet Detection; Single-Laboratory Validation", Vol. 94(2); pp. 459-466

Figure 10:
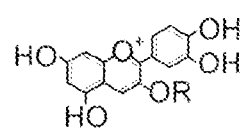
FIG. 10 provides the chemical structures of five anthocyanins identified in cranberry fruit extract (E1) present in the extract in an amount of 1.90 mg/g total anthocyanins.
Figure 10:
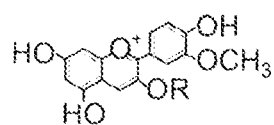
Figure 10:
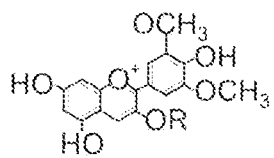

(2011). These compounds are illustrated in FIG. 10. No anthocyanins were detected in E2.

TABLE 5

Amount of five anthocyanins calculated in E1

| mg/g | R1—25 mg/mL | R1—50 mg/mL |
|---|---|---|
| C3-Gla | 0.506 | 0.503 |
| C3-Ara | 0.276 | 0.275 |
| P3-Gla | 0.591 | 0.587 |
| P3-Ara | 0.200 | 0.195 |
| Mal-3-Gla | 0.330 | 0.331 |

Examples—Bioassay

Extracts of cranberry fruit (E1) and cranberry leaf (E2) were prepared with food-grade ethanol, and then filtered and dried as described above. Research grade reagents were used for the rest of the assay preparations. Extracts were dissolved in dimethyl sulfoxide ('DMSO') to a final concentration of 50 mg/mL, and then diluted in appropriate buffer for each bioassay to working concentrations.

Example 4—COX-1 and COX-2 Inhibition

Figure 12:
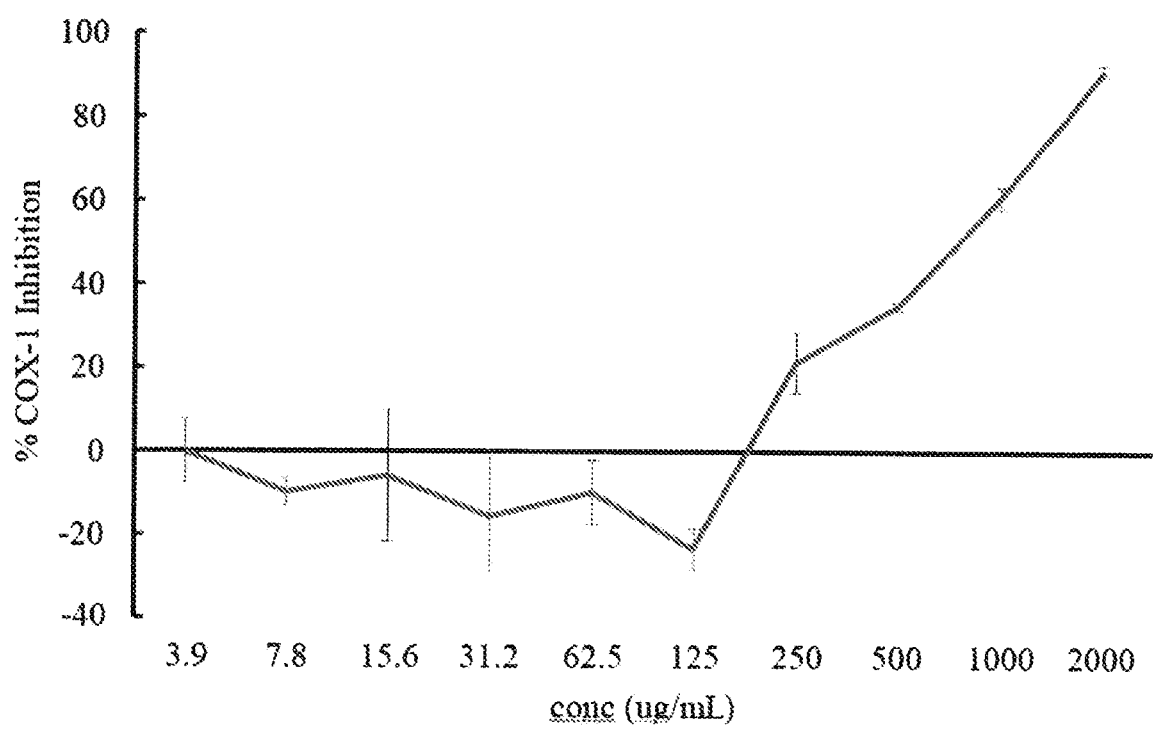
FIG. 12 is a graph illustrating percentage COX-1 inhibition using cranberry fruit extract (E1) at various concentrations.
Figure 13:
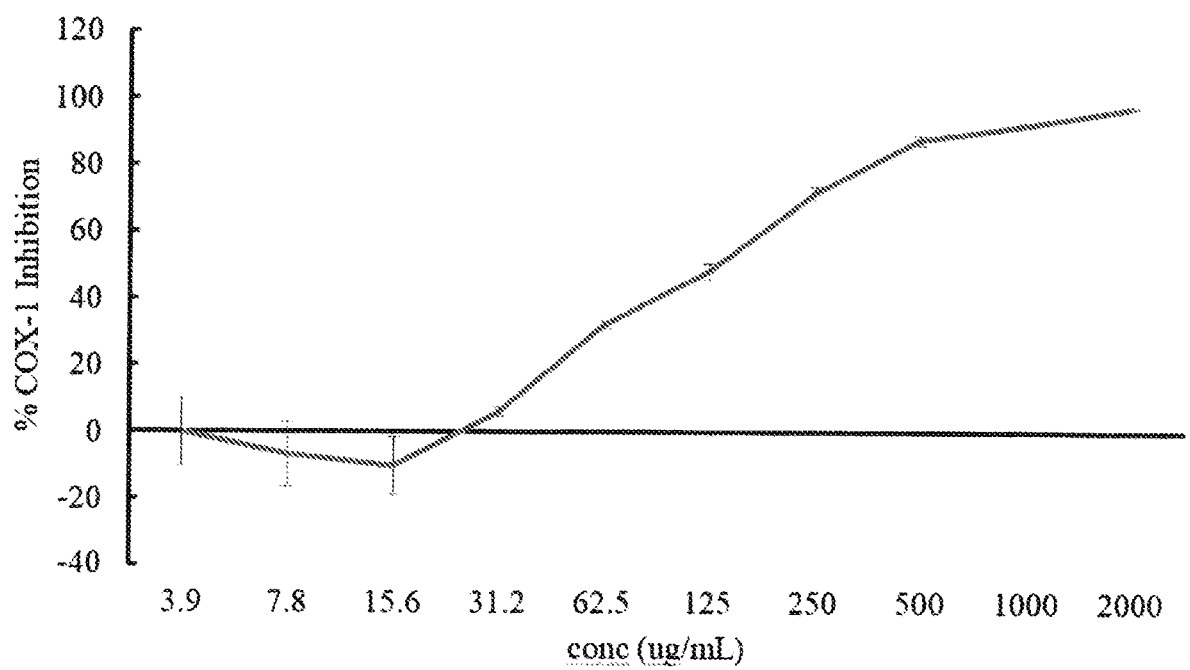
FIG. 13 is a graph illustrating percentage COX-1 inhibition using cranberry leaf extract (E2) at various concentrations.

Cranberry fruit extract (E1) and cranberry leaf extract (E2) were tested for COX-1 inhibition using the cyclooxygenase-1 ('COX-1') Inhibitor Screening Kit (catalog #K548) from BioVision (Milpitas, California, US). This screening kit measures the production of the organic peroxide prostaglandin G2, a product generated by the COX enzyme, over a time course. Extracts were dissolved to working concentrations in DMSO with COX Assay Buffer to a final concentration of 5% DMSO. SC-560 COX-1 inhibitor was used as a positive control. COX-1 enzyme was reconstituted in sterile water and stored at −80° C. COX cofactor and arachidonic acid solutions were diluted just prior to use. COX probe, COX cofactor, and COX-1 enzyme solution were added to the test samples and controls before the arachidonic acid solution was quickly added to start the reaction. Fluorescence was measured every minute for 10 minutes at the following wavelengths: excitation −535 nm, emission 590 nm. The slope of the linear portion of the curve (FIG. 5) was deduced and percent inhibition of the uninhibited control was calculated. Referring to FIGS. 12 and 13, various degrees of COX-1 inhibition were observed, depending on the concentration of cranberry fruit extract E1 or cranberry leaf extract E2. Cranberry fruit extract E1 COX-1 inhibition was observed to be from about 175 µg/mL to at least about 2000 µg/mL, more particularly from about 175 µg/mL to about 1000 µg/mL, with an $IC_{50}$ of 790 µg/mL. Cranberry leaf extract E2 COX-1 inhibition was observed to be from about 30 µg/mL to at least about 2000 µg/mL, more particularly from about 50 µg/mL to about 500 µg/mL, with an $IC_{50}$ of 135 µg/mL, showing the cranberry leaf extract E2 to have better COX-1 inhibition activity than the cranberry fruit extract E1.

Figure 14:
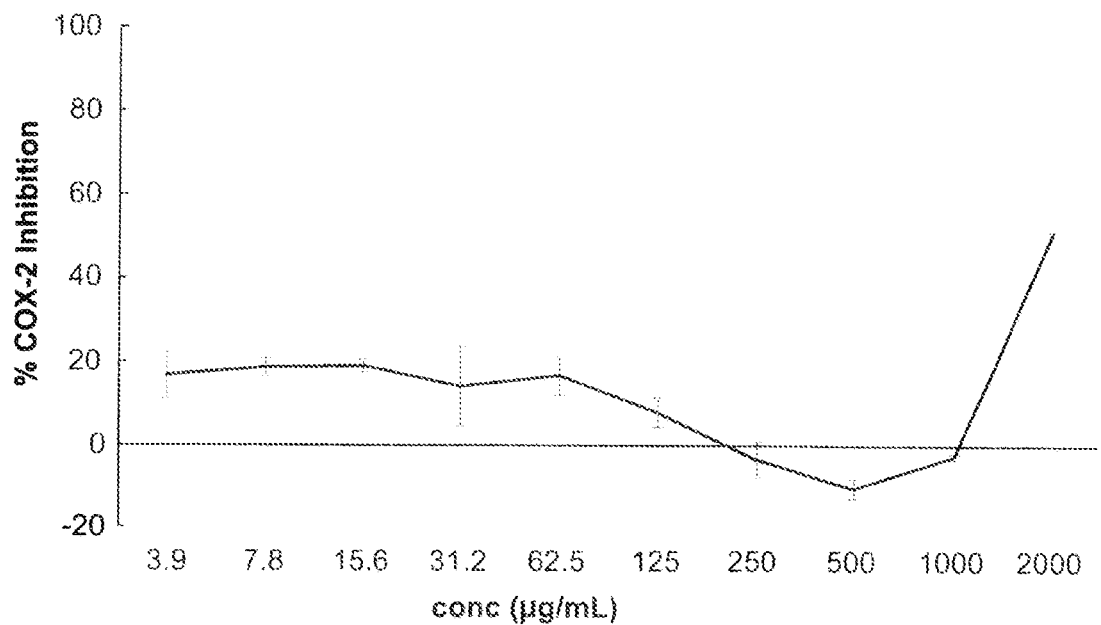
FIG. 14 is a graph illustrating percentage COX-2 inhibition using cranberry fruit extract (E1) at various concentrations.
Figure 15:
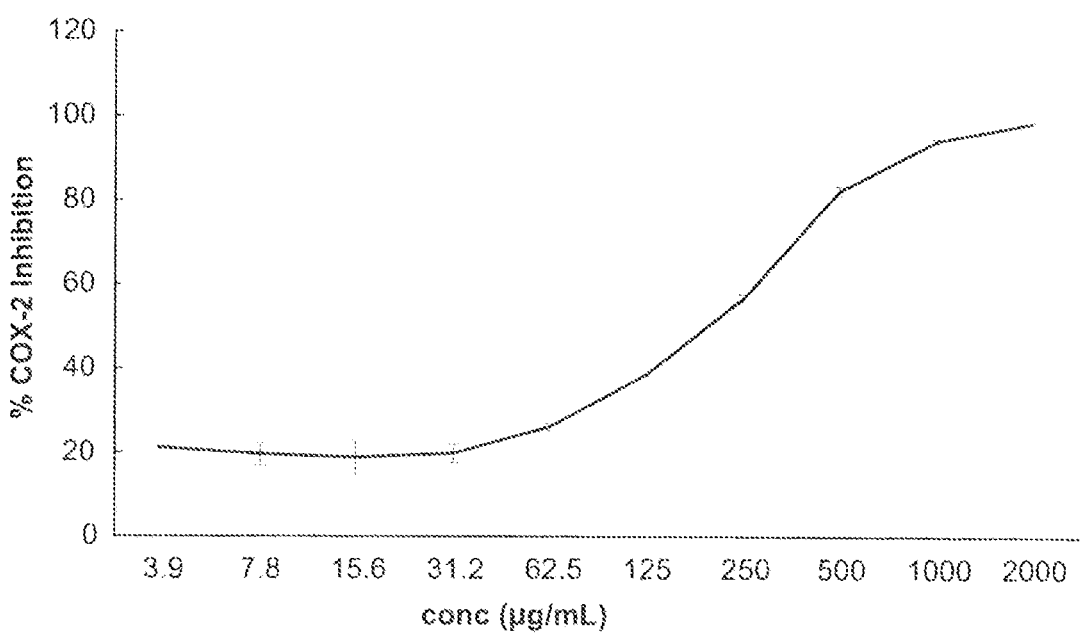
FIG. 15 is a graph illustrating percentage COX-2 inhibition using cranberry leaf extract (E2) at various concentrations.

Cranberry fruit extract (E1) and cranberry leaf extract (E2) were tested for COX-2 inhibition using the cyclooxygenase-2 ('COX-2') Inhibitor Screening Kit (catalog #K547) from BioVision (Milpitas, California, US). This screening kit measures the production of the organic peroxide prostaglandin G2, a product generated by the COX enzyme, over a time course. Extracts were dissolved to working concentrations in DMSO with COX Assay Buffer to a final concentration of 10% DMSO. Celecoxib nonsteroidal anti-inflammatory drug ('NSAID') was used as a positive control. COX-2 enzyme was reconstituted in sterile water and stored at −80° C. COX cofactor and arachidonic acid solutions were diluted just prior to use. COX probe, COX cofactor, and COX-1 enzyme solution were added to the test samples and controls before the arachidonic acid solution was quickly added to start the reaction. Fluorescence was measured every minute for 10 minutes at the following wavelengths: excitation −535 nm, emission 590 nm. The slope of the linear portion of the curve (FIG. 6) was deduced and percent inhibition of the uninhibited control was calculated. Referring to FIGS. 14 and 15, various degrees of COX-2 inhibition were observed, depending on the concentration of cranberry fruit extract E1 or cranberry leaf extract E2. Cranberry fruit extract E1 COX-2 inhibition was observed to be from about 1000.0 µg/mL to at least about 2000.0 µg/mL, with an $IC_{50}$ of 1978.0 µg/mL. Cranberry leaf extract COX-2 inhibition was observed to be from about 1.0 µg/mL to at least about 2000.0 µg/mL, more particularly from about 30.0 µg/mL to about 500.0 µg/mL, with an $IC_{50}$ of 205.0 µg/mL, showing the cranberry leaf extract E2 to have better COX-2 inhibition activity than the cranberry fruit extract E1. Accordingly, based on the results presented herein, cranberry leaf extract E2 may have reasonable activities in ameliorating the activity or release of COX-1 and COX-2, suggesting its usage in inflammatory diseases mediated by COX-1 and COX-2.

Example 5—5-LOX Inhibition

Cranberry fruit extract (E1) and cranberry leaf extract (E2) were tested for 5-LOX inhibition using the Lipoxygenase Inhibitor Screening Assay Kit (available from Cayman Chemical, Ann Arbor, Michigan, US) and potato 5-Lipoxygenase enzyme (available from Cayman Chemical). This kit measures hydroperoxides produced in the lipoxygenation reaction.

The extracts were dissolved in methanol to final working concentrations. 5-LOX enzyme, Chromagen, and Linoleic Acid solutions were prepared immediately before use. Nordihydroguaiaretic acid ('NDGA') was used as a positive control. 5-LOX enzyme was added to the test samples and controls and incubated for five minutes at room temperature to allow for enzyme/inhibitor interaction. Linoleic acid substrate was added to the plate to initiate the reaction, and the plate was then shaken at room temperature for 10 minutes. Chromagen was added to visualize the hydroperoxides formed during the reaction and the plate was shaken at room temperature for another five minutes. The absorbance was then read at 492 nm. Percent inhibition of the extract concentration was calculated in comparison to the uninhibited control wells.

Figure 16:
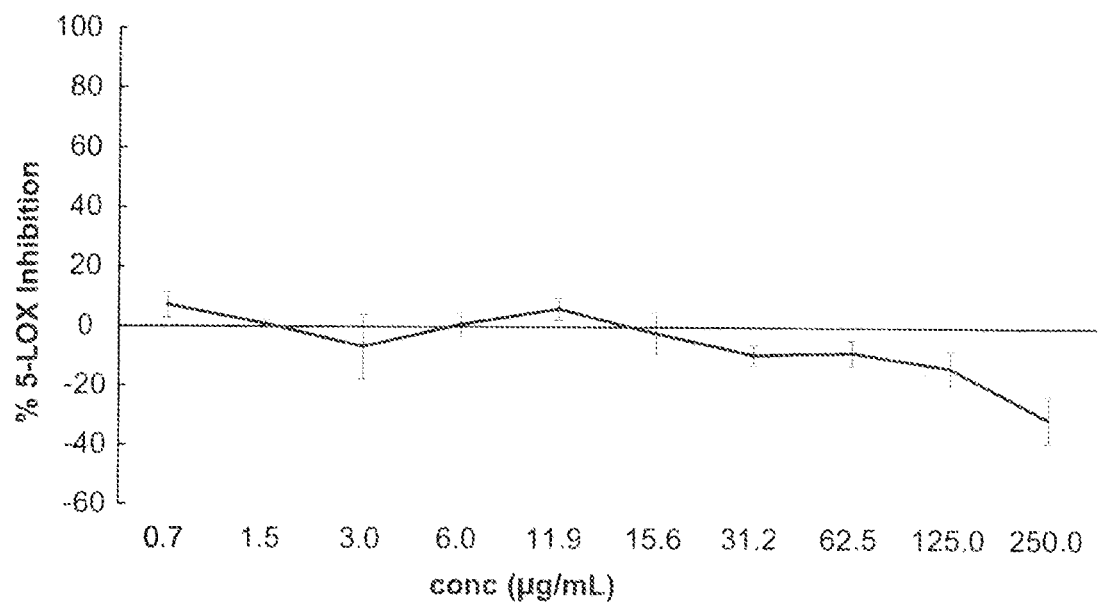
FIG. 16 is a graph illustrating percentage 5-LOX inhibition using cranberry fruit extract (E1) at various concentrations.
Figure 17:
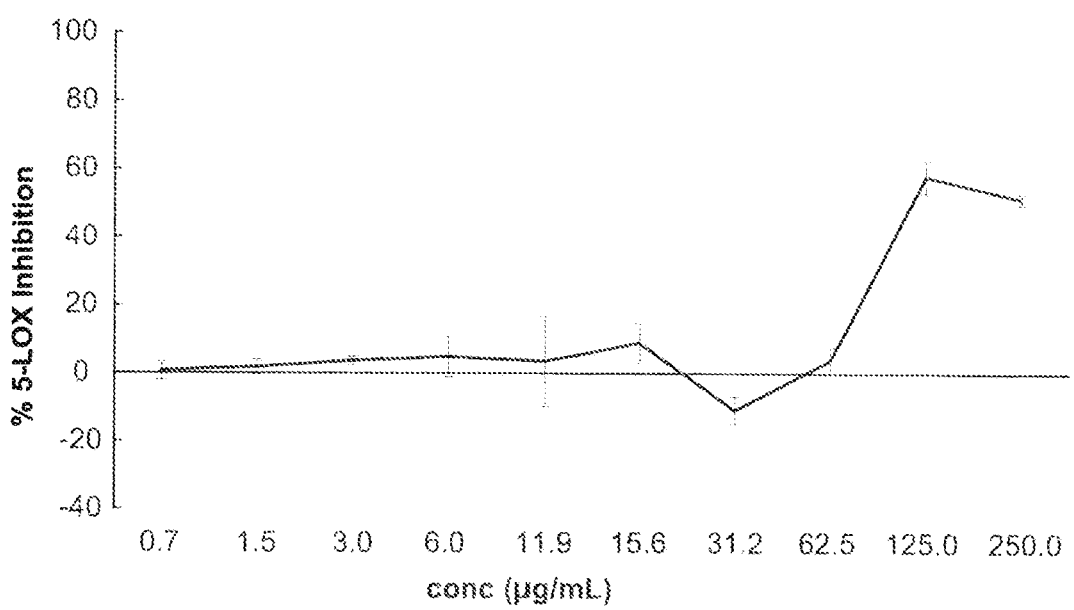
FIG. 17 is a graph illustrating percentage 5-LOX inhibition using cranberry leaf extract (E2) at various concentrations.

Cranberry fruit extract (E1) and cranberry leaf extract (E2) were tested for 5-LOX inhibition activity at 10 different concentrations (0.7, 1.5, 3.0, 6.0, 11.9, 15.6, 31.2, 62.5, 125.0 and 250.0 µg/mL). NDGA was used as a positive control at 100 µM with a 100% 5-LOX enzyme inhibition. As illustrated in FIG. 16, no inhibition was observed for the cranberry fruit extract E1. Referring to FIG. 17, cranberry leaf extract E2 5-LOX inhibition was observed to be from about 60.0 µg/mL to at least about 250.0 µg/mL, more particularly from about 60.0 µg/mL to about 150.0 µg/mL, with an $IC_{50}$ of 116 μg/mL observed for the cranberry leaf extract. Accordingly, based on the results presented herein, cranberry leaf extract E2 may have reasonable activities in ameliorating the activity or release of 5-LOX, suggesting its usage in inflammatory diseases mediated by 5-LOX.

The above data illustrates that the botanical extract of the leaf of *Vaccinium macrocarpon* has one or more compounds that exhibit anti-inflammatory activity. More particularly, the cranberry leaf extract may have reasonable activities in ameliorating the activity or release of COX-1, COX-2, and/or 5-LOX.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Further, unless defined otherwise, all technical and scientific terms used herein have the same meaning as commonly understood to one of ordinary skill in the art to which this invention belongs. Consequently, it is not intended that this invention be limited to the specific embodiments disclosed herein, but that it covers all modifications and alternatives coming within the true scope and spirit of the invention as embodied in the attached claims.

We claim:

1. A composition comprising:
a botanical extract of a leaf of *Vaccinium macrocarpon*, wherein the botanical extract is present in an amount of about 50.0 μg/mL to about 500.0 μg/mL,
wherein the botanical extract comprises at least isoquercetin and kaempferol and is free of anthocyanins,
wherein the extract is obtained by extracting dried ground cranberry leaf powder with a solvent of ethanol in water and evaporating the solvent,
a pharmaceutically acceptable carrier,
wherein the composition exhibits anti-inflammatory activity.

2. The composition according to claim 1, wherein the composition inhibits COX-1 activity.

3. The composition according to claim 1, wherein the composition inhibits COX-2 activity.

4. The composition according to claim 1, wherein the composition inhibits 5-LOX activity.

5. The composition according to claim 1, wherein the composition inhibits COX-1 activity, COX-2 activity, and 5-LOX activity.

6. The composition according to claim 1, wherein the composition is a dietary supplement.

7. The dietary supplement according to claim 1, wherein the composition is a topical composition.

* * * * *